US010410417B2

(12) United States Patent
Chen et al.

(10) Patent No.: US 10,410,417 B2
(45) Date of Patent: *Sep. 10, 2019

(54) SYSTEM AND METHOD FOR NAVIGATING A TOMOSYNTHESIS STACK USING SYNTHESIZED IMAGE DATA

(71) Applicant: HOLOGIC, INC., Marlborough, MA (US)

(72) Inventors: Jin-Long Chen, Santa Clara, CA (US); Haili Chui, Fremont, CA (US); Nikolaos Gkanatsios, Danbury, CT (US); Kevin Kreeger, Sunnyvale, CA (US); Julian Marshall, Los Altos, CA (US); David Mislan, Lexington, MA (US); Mark A. Prazer, San Jose, CA (US); Xiangwei Zhang, Fremont, CA (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/794,635

(22) Filed: Oct. 26, 2017

(65) Prior Publication Data
US 2018/0047211 A1  Feb. 15, 2018

Related U.S. Application Data

(63) Continuation of application No. 14/376,530, filed as application No. PCT/US2013/025993 on Feb. 13, 2013, now Pat. No. 9,805,507.
(Continued)

(51) Int. Cl.
*G06T 19/00* (2011.01)
*A61B 6/00* (2006.01)
(Continued)

(52) U.S. Cl.
CPC ............ *G06T 19/003* (2013.01); *A61B 6/025* (2013.01); *A61B 6/466* (2013.01); *A61B 6/502* (2013.01);
(Continued)

(58) Field of Classification Search
CPC ..... G06T 19/003; G06T 7/0012; A61B 6/025; A61B 6/466; A61B 6/502; G06F 3/04815; G06F 3/04842
See application file for complete search history.

(56) References Cited

U.S. PATENT DOCUMENTS 3,502,878 A   3/1970   Stewart et al.
3,863,073 A   1/1975   Wagner
(Continued)

FOREIGN PATENT DOCUMENTS

DE   102010009295   8/2011
EP         775467   5/1997
(Continued)

OTHER PUBLICATIONS

Liyakathunisa et al, "A Novel and Efficient Lifting Scheme based Super Resolution Reconstruction for Early Detection of Cancer in Low Resolution Mammogram Images", 2011, International Journal of Biometrics and Bioinformatics (IJBB), vol. 5, Issue 2, 26 pages (Year: 2011).*
(Continued)

*Primary Examiner* — David F Dunphy
(74) *Attorney, Agent, or Firm* — Vista IP Law Group, LLP

(57) ABSTRACT

A system and method for displaying and navigating breast tissue is configured for or includes obtaining a plurality of 2D and/or 3D images of a patient's breast; generating a synthesized 2D image of the breast from the obtained images; displaying the synthesized 2D image; receiving a
(Continued)

user command, or otherwise detecting through a user interface, a user selection or other indication of an object or region in the synthesized 2D image; and displaying at least a portion of one or more images from the plurality, including a source image and/or most similar representation of the user selected or indicated object or region.

20 Claims, 11 Drawing Sheets

Related U.S. Application Data

(60) Provisional application No. 61/597,958, filed on Feb. 13, 2012.

(51) Int. Cl.
  *G06F 3/0484* (2013.01)
  *A61B 6/02* (2006.01)
  *G06F 3/0481* (2013.01)
  *G06T 7/00* (2017.01)

(52) U.S. Cl.
  CPC ...... *G06F 3/04815* (2013.01); *G06F 3/04842* (2013.01); *G06T 7/0012* (2013.01); *G06T 2207/30068* (2013.01)

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 3/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,657,362 A | 8/1997 | Giger et al. |
| 5,668,889 A | 9/1997 | Hara |
| 5,712,890 A * | 1/1998 | Spivey ............... A61B 6/032 378/37 |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz |
| 5,872,828 A | 2/1999 | Niklason |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,986,662 A | 11/1999 | Argiro |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,272,207 B1 | 8/2001 | Tang |
| 6,289,235 B1 | 9/2001 | Webber et al. |
| 6,292,530 B1 | 9/2001 | Yavus |
| 6,327,336 B1 | 12/2001 | Gingold et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,442,288 B1 | 8/2002 | Haerer |
| 6,459,925 B1 | 10/2002 | Nields et al. |
| 6,463,181 B2 | 10/2002 | Duarte |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,912,319 B1 | 5/2005 | Barnes |
| 6,940,943 B2 | 9/2005 | Claus |
| 6,978,040 B2 | 12/2005 | Berestov |
| 6,999,554 B2 | 2/2006 | Mertelmeier |
| 7,025,725 B2 | 4/2006 | Dione et al. |
| 7,110,490 B2 | 9/2006 | Eberhard |
| 7,110,502 B2 | 9/2006 | Tsuji |
| 7,123,684 B2 | 10/2006 | Jing et al. |
| 7,127,091 B2 | 10/2006 | OpDeBeek |
| 7,142,633 B2 | 11/2006 | Eberhard |
| 7,245,694 B2 | 7/2007 | Jing et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,702,142 B2 | 4/2010 | Ren et al. |

(56) References Cited

U.S. PATENT DOCUMENTS

| | | | |
|---|---|---|---|
| 7,760,924 B2 | 7/2010 | Ruth et al. | |
| 7,831,296 B2 | 11/2010 | DeFreitas et al. | |
| 8,044,972 B2 | 10/2011 | Hall et al. | |
| 8,051,386 B2 | 11/2011 | Rosander et al. | |
| 8,126,226 B2* | 2/2012 | Bernard | G06T 11/006 382/128 |
| 8,155,421 B2 | 4/2012 | Ren et al. | |
| 8,165,365 B2 | 4/2012 | Bernard et al. | |
| 8,571,289 B2 | 10/2013 | Ruth | |
| 8,712,127 B2 | 4/2014 | Ren et al. | |
| 8,897,535 B2 | 11/2014 | Ruth et al. | |
| 8,983,156 B2 | 3/2015 | Periaswamy et al. | |
| 9,084,579 B2 | 7/2015 | Ren et al. | |
| 9,456,797 B2 | 10/2016 | Ruth et al. | |
| 9,805,507 B2* | 10/2017 | Chen | A61B 6/025 |
| 9,811,758 B2 | 11/2017 | Ren et al. | |
| 2001/0038861 A1 | 11/2001 | Hsu et al. | |
| 2002/0012450 A1 | 1/2002 | Tsujii | |
| 2002/0050986 A1 | 5/2002 | Inoue | |
| 2002/0075997 A1 | 6/2002 | Unger et al. | |
| 2003/0007598 A1 | 1/2003 | Wang | |
| 2003/0018272 A1 | 1/2003 | Treado et al. | |
| 2003/0026386 A1 | 2/2003 | Tang | |
| 2003/0073895 A1 | 4/2003 | Nields et al. | |
| 2003/0095624 A1 | 5/2003 | Eberhard et al. | |
| 2003/0128893 A1 | 7/2003 | Castorina | |
| 2003/0169847 A1 | 9/2003 | Karellas | |
| 2003/0194050 A1 | 10/2003 | Eberhard | |
| 2003/0194121 A1 | 10/2003 | Eberhard et al. | |
| 2003/0210254 A1 | 11/2003 | Doan | |
| 2003/0212327 A1 | 11/2003 | Wang | |
| 2003/0215120 A1 | 11/2003 | Uppaluri | |
| 2004/0008809 A1 | 1/2004 | Webber | |
| 2004/0008901 A1 | 1/2004 | Avinash | |
| 2004/0047518 A1 | 3/2004 | Tiana | |
| 2004/0052328 A1 | 3/2004 | Saboi | |
| 2004/0066884 A1 | 4/2004 | Hermann Claus et al. | |
| 2004/0066904 A1 | 4/2004 | Eberhard et al. | |
| 2004/0070582 A1 | 4/2004 | Smith et al. | |
| 2004/0094167 A1 | 5/2004 | Brady | |
| 2004/0101095 A1 | 5/2004 | Jing et al. | |
| 2004/0109529 A1 | 6/2004 | Eberhard et al. | |
| 2004/0171986 A1 | 9/2004 | Tremaglio, Jr. et al. | |
| 2004/0267157 A1 | 12/2004 | Miller et al. | |
| 2005/0049521 A1 | 3/2005 | Miller et al. | |
| 2005/0063509 A1 | 3/2005 | Defreitas et al. | |
| 2005/0078797 A1 | 4/2005 | Danielsson et al. | |
| 2005/0105679 A1 | 5/2005 | Wu et al. | |
| 2005/0113681 A1 | 5/2005 | DeFreitas | |
| 2005/0113715 A1 | 5/2005 | Schwindt et al. | |
| 2005/0135555 A1 | 6/2005 | Claus | |
| 2005/0135664 A1 | 6/2005 | Kaufhold | |
| 2005/0226375 A1 | 10/2005 | Eberhard | |
| 2006/0018526 A1 | 1/2006 | Avinash | |
| 2006/0030784 A1 | 2/2006 | Miller et al. | |
| 2006/0074288 A1 | 4/2006 | Kelly et al. | |
| 2006/0098855 A1 | 5/2006 | Gkanatsios | |
| 2006/0129062 A1 | 6/2006 | Nicoson et al. | |
| 2006/0155209 A1 | 7/2006 | Miller et al. | |
| 2006/0291618 A1 | 12/2006 | Eberhard et al. | |
| 2007/0030949 A1 | 2/2007 | Jing et al. | |
| 2007/0036265 A1 | 2/2007 | Jing et al. | |
| 2007/0052700 A1 | 3/2007 | Wheeler et al. | |
| 2007/0076844 A1 | 4/2007 | Defreitas et al. | |
| 2007/0223651 A1 | 9/2007 | Wagenaar et al. | |
| 2007/0225600 A1 | 9/2007 | Weibrecht et al. | |
| 2007/0242800 A1 | 10/2007 | Jing et al. | |
| 2008/0045833 A1 | 2/2008 | Defreitas et al. | |
| 2008/0130979 A1 | 6/2008 | Ren | |
| 2008/0187095 A1 | 8/2008 | Boone et al. | |
| 2009/0003519 A1 | 1/2009 | Defreitas et al. | |
| 2009/0005668 A1 | 1/2009 | West et al. | |
| 2009/0010384 A1 | 1/2009 | Jing et al. | |
| 2009/0034684 A1 | 2/2009 | Bernard et al. | |
| 2009/0080594 A1 | 3/2009 | Brooks et al. | |
| 2009/0080602 A1 | 3/2009 | Brooks et al. | |
| 2009/0080765 A1 | 3/2009 | Bernard et al. | |
| 2009/0123052 A1 | 5/2009 | Ruth | |
| 2009/0135997 A1 | 5/2009 | Defreitas et al. | |
| 2009/0238424 A1 | 9/2009 | Arakita | |
| 2009/0268865 A1 | 10/2009 | Ren et al. | |
| 2009/0296882 A1 | 12/2009 | Gkanatsios et al. | |
| 2009/0304147 A1 | 12/2009 | Jing et al. | |
| 2010/0054400 A1 | 3/2010 | Ren et al. | |
| 2010/0086188 A1 | 4/2010 | Ruth et al. | |
| 2010/0135558 A1 | 6/2010 | Ruth et al. | |
| 2010/0195882 A1 | 8/2010 | Ren et al. | |
| 2010/0259645 A1 | 10/2010 | Kaplan | |
| 2011/0069906 A1 | 3/2011 | Park | |
| 2011/0109650 A1 | 5/2011 | Kreeger et al. | |
| 2011/0110576 A1 | 5/2011 | Kreeger et al. | |
| 2011/0178389 A1 | 7/2011 | Kumar et al. | |
| 2011/0234630 A1 | 9/2011 | Batman et al. | |
| 2011/0242092 A1 | 10/2011 | Kashiwagi | |
| 2012/0293511 A1 | 11/2012 | Mertelmeier | |
| 2014/0327702 A1 | 11/2014 | Kreeger et al. | |
| 2015/0317538 A1 | 11/2015 | Ren et al. | |
| 2018/0137385 A1 | 5/2018 | Ren | |
| 2019/0043456 A1 | 2/2019 | Kreeger et al. | |

FOREIGN PATENT DOCUMENTS

| | | | |
|---|---|---|---|
| EP | 982001 | 3/2000 | |
| EP | 1428473 | 6/2004 | |
| EP | 2215600 | 8/2010 | |
| EP | 2301432 | 3/2011 | |
| JP | 2003-189179 | 7/2003 | |
| JP | 2007-536968 | 12/2007 | |
| JP | 2009-207545 | 9/2009 | |
| WO | WO 90/05485 | 5/1990 | |
| WO | WO 9816903 | 4/1998 | |
| WO | WO 00/51484 | 9/2000 | |
| WO | WO 03020114 | 3/2003 | |
| WO | WO 2005051197 | 6/2005 | |
| WO | WO 2005110230 | 11/2005 | |
| WO | WO 2005112767 | 12/2005 | |
| WO | WO 2006055830 | 5/2006 | |
| WO | WO 2006058160 | 6/2006 | |
| WO | WO 2008047270 | 4/2008 | |
| WO | WO 2010059920 | 5/2010 | |
| WO | WO 2011008239 | 1/2011 | |
| WO | WO 2011/065950 * | 6/2011 ............... H05G 1/64 |
| WO | WO 2011065950 | 6/2011 | |
| WO | WO 2011073864 | 6/2011 | |
| WO | WO 2011091300 | 7/2011 | |
| WO | WO 2012063653 | 5/2012 | |

OTHER PUBLICATIONS

Mikko Lilja, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway NJ, Oct. 25, 2008.

Pediconi, "Color-coded automated signal intensity-curve for detection and characterization of breast lesions: Preliminary evaluation of new software for MR-based breast imaging," International Congress Series 1281 (2005) 1081-1086.

Heang-Ping, Roc "Study of the effect of stereoscopic imaging on assessment of breast lesions," Medical Physics, vol. 32, No. 4, Apr. 2005.

Amendment Response to Final Office Action for U.S. Appl. No. 12/276,006 dated Mar. 24, 2010 (6 pages).

Amendment Response to Non-Final Office Action for U.S. Appl. No. 12/276,006 dated Sep. 28, 2009 (8 pages).

Final Office Action dated Jan. 20, 2010 for U.S. Appl. No. 12/276,006.

Non-Final Office Action dated Jun. 25, 2009 for U.S. Appl. No. 12/276,006.

Amendment Resonse after Final Office Action for U.S. Appl. No. 12/471,981 dated Apr. 3, 2013 (6 pages).

(56) References Cited

OTHER PUBLICATIONS

Amendment Response to Non-Final Office Action for U.S. Appl. No. 12/471,981 dated Dec. 10, 2012 (6 pages).
Non-Final Office Action dated Feb. 13, 2013 for U.S. Appl. No. 12/471,981.
Non-Final Office Action dated Aug. 10, 2012 for U.S. Appl. No. 12/471,981.
Amendment Response to Non-Final Office Action for U.S. Appl. No. 14/044,959 dated May 13, 2014 (8 pages).
Non-Final Office Action dated Feb. 13, 2014 for U.S. Appl. No. 14/044,959.
Foreign Office Action for CN Application No. 200980101409.X dated Jun. 26, 2014.
Foreign Office Action for EP Patent Application No. 09796173.4 dated Apr. 11, 2014.
Foreign Office Action for JP Patent Application No. 2011-537644 dated Jul. 29, 2013.
Foreign Office Action for JP Patent Application No. 2014-047021 dated Jan. 21, 2015.
International Search Report for International Publication No. PCT/US2009/065288 dated Jan. 29, 2014.
International Preliminary Report on Patentability for International Publication No. PCT/US2012/066526 dated May 27, 2014.
PCT Notification of International Search Report and Written Opinion for PCT/US2012/066526, Applicant HOLOGIC, INC., dated Feb. 6, 2013 (7 pages).
International Preliminary Report on Patentability for International Publication No. PCT/US2013/025993 dated Aug. 19, 2014.
International Search Report and Written Opinion for International Publication No. PCT/US2013/025993 dated Apr. 26, 2013.
Foreign office action from JP 2014-543604 dated Oct. 4, 2016.
Extended EP Search Report for EP Application No. 13749870.5 dated Oct. 7, 2015, 7 pages.
Extended EP Search Report for EP Application No. 12851085.6, dated Jan. 6, 2015, 6 pages.
Giger et al. "Development of a smart workstation for use in mammography", in Proceedings of SPIE, vol. 1445 (1991), pp. 101 103; 4 pages.
Giger et al., "An Intelligent Workstation for Computer-aided Diagnosis", in RadioGraphics, May 1993, 13:3 pp. 647 656; 10 pages.
Non final office action dated Jan. 22, 2016 for U.S. Appl. No. 14/360,389.
"Predicting tumour location by simulating large deformations of the breast using a 3D finite element model and nonlinear elasticity" by P. Pathmanathan et al., Medical Image Computing and Computer-Assisted Intervention, pp. 217-224, vol. 3217 (2004).
"ImageParser: a tool for finite element generation from three-dimensional medical images" by H. M. Yin et al., BioMedical Engineering OnLine. 3:31, pp. 1-9, Oct. 1, 2004.
"Biomechanical 3-D Finite Element Modeling of the Human Breast Using MRI Data" by A. Samani et al. IEEE Transactions on Medical Imaing, vol. 20, No. 4, pp. 271-279. 2001.
"Mammogram synthesis using a 3D simulation. I. breast tissue model and image acquisition simulation" by Bakic et al., Medical Physics. 29, pp. 2131-2139 (2002).
Non Final Office action dated Nov. 20, 2015 for U.S. Appl. No. 14/549,604.
Office Action dated Mar. 10, 2017 for Canadian Application No. 2,702,782, Owner Hologic, Inc., based on PCT/US2009/065288, 3 pages.
Office Action dated Jan. 11, 2017 for Japanese Patent Application No. 2014-556824, Applicant Hologic, Inc., including English Translation provided by Japanese associate, 12 pages.
Computer generated translation of Foreign Patent Reference JP 2003-189179 A, published Jul. 4, 2003, 16 pages.
Response to Non Final Office action dated May 23, 2016 for U.S. Appl. No. 14/360,389.
Final Office Action dated Jul. 5, 2016 for U.S. Appl. No. 14/360,389.
Response to Final Office Action dated Aug. 15, 2016 for U.S. Appl. No. 14/360,389.
Advisory Action dated Aug. 24, 2016 for U.S. Appl. No. 14/360,389.
Pre-Appeal Brief Request for Review submitted Oct. 4, 2016 for U.S. Appl. No. 14/360,389.
Appeal Brief submitted Dec. 4, 2016 for U.S. Appl. No. 14/360,389.
Examiners Answer to Appeal Brief dated Jan. 31, 2017 for U.S. Appl. No. 14/360,389.
Reply Brief submitted Mar. 6, 2017 for U.S. Appl. No. 14/360,389.
Decision on Appeal dated Nov. 8, 2017 for U.S. Appl. No. 14/360,389.
Non-Final Office Action dated Mar. 9, 2017 for U.S. Appl. No. 15/088,844.
Notice of Allowance for U.S. Appl. No. 15/088,844 dated Jun. 29, 2017.
Notice of Allowance for U.S. Appl. No. 15/088,844 dated Mar. 28 2017.
International Preliminary Report on Patentability for International Publication No. PCT/US2009/065288 dated Feb. 18, 2014.
Notice of Allowance dated Jan. 22, 2018 for U.S. Appl. No. 14/360,389.
Office action dated Feb. 1, 2018 for U.S. Appl. No. 15/802,225.
Office Action dated Feb. 19, 2018 for EP Application 12851085.6, Applicant Hologic, Inc. 5 pp.
Extended EP Search Report for EP Application No. 17176956.5 dated Apr. 3, 2018, 7 pages.
Non Final office Action dated Jan. 25, 2019 for U.S. Appl. No. 16/013,782.
European search report in connection with corresponding European patent application No. EP 06255790, dated Aug. 17, 2007.
European search report in connection with counterpart European Patent Application No. 05824734, dated May 9, 2011.
PCT International Search Report and Written Opinion dated Sep. 25, 2008, for International Application No. PCT/US2005/041941, Applicant Hologic, Inc., 8 pages.
Amendment After Non-Final Office Action filed Apr. 12, 2019 for U.S. Appl. No. 16/013,782.
Non Final Office Action dated Sep. 21, 2016 for U.S. Appl. No. 14/744,930.
Response to Non Final Office action filed Dec. 14, 2016 for U.S. Appl. No. 14/744,930.
Final Office Action dated Mar. 31, 2017 for U.S. Appl. No. 14/744,930.
Response to Final Office action filed Aug. 21, 2017 for U.S. Appl. No. 14/744,930.
Non Final Office action dated May 18, 2018 for U.S. Appl. No. 15/804,915.
Response to Non Final Office Action filed Aug. 20, 2018 for U.S. Appl. No. 15/804,915.

\* cited by examiner

SYSTEM AND METHOD FOR NAVIGATING A TOMOSYNTHESIS STACK USING SYNTHESIZED IMAGE DATA

RELATED APPLICATION DATA

This application is a continuation of U.S. patent application Ser. No. 14/376,530, now issued as U.S. Pat. No. 9,805,507, which is a National Phase Entry under 35 U.S.C. § 371 of International Patent Application No. PCT/US2013/025993, having an international filing date of Feb. 13, 2013, which claims the benefit of priority under 35 U.S.C. § 119 to U.S. Provisional Patent Application No. 61/597,958, filed Feb. 13, 2012, and which is hereby incorporated by reference in its entirety.

FIELD

The inventions disclosed herein pertain to breast imaging using tomosynthesis, and more specifically to a system and method for guiding the navigation of a tomosynthesis data set, which employs a synthesized 2D image that is obtained by importing relevant data from the tomosynthesis data set into the synthesized image, and then using the 2D image to navigate the tomosynthesis data.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired images, and provide other benefits as well. Further, substantial attention and technological development has been dedicated towards obtaining three-dimensional images of the breast, using methods such as breast tomosynthesis. In contrast to the 2D images generated by legacy mammography systems, breast tomosynthesis systems construct a 3D image volume from a series of 2D projection images, each projection image obtained at a different angular displacement of an x-ray source relative to the image detector as the x-ray source is scanned over the detector. The constructed 3D image volume is typically presented as a plurality of slices of image data, the slices being geometrically reconstructed on planes parallel to the imaging detector. The reconstructed tomosynthesis slices reduce or eliminate the problems caused by tissue overlap and structure noise present in single slice, two-dimensional mammography imaging, by permitting a medical professional (e.g., a radiologist) to scroll through the image slices to view underlying structures.

Tomosynthesis systems have recently been developed for breast cancer screening and diagnosis. In particular, Hologic, Inc. (www.hologic.com), has developed a fused, multimode mammography/tomosynthesis system that acquires one or both types of mammogram and tomosynthesis images, either while the breast remains immobilized or in different compressions of the breast. Other companies have proposed the introduction of systems which are dedicated to tomosynthesis imaging; i.e., which do not include the ability to also acquire a mammogram.

However, systems restricted to tomosynthesis acquisition and image display may present an obstacle to acceptance of the tomosynthesis imaging technology, as medical professionals have grown accustomed to screening and analysis of conventional 2D mammogram images. In particular, mammograms provide good visualization of micro-calcifications, and can offer higher spatial resolution when compared with tomosynthesis images. While tomosynthesis images provided by dedicated breast tomosynthesis systems have other desirable characteristics, e.g., better isolation and visualization of structures in the breast, such systems do not leverage the existing interpretation expertise of medical professionals.

Examples of systems and methods that leverage existing medical expertise in order to facilitate the transition to tomosynthesis technology are described in U.S. Pat. No. 7,760,924, which is hereby incorporated by reference in its entirety. In particular, U.S. Pat. No. 7,760,924 describes a method of generating a synthesized 2D image, which may be displayed along with tomosynthesis projection or reconstructed images, in order to assist in screening and diagnosis.

SUMMARY

According to one aspect of the inventions disclosed and described herein, a system and method for processing, displaying and navigating breast tissue information is provided, wherein the system is configured for, and the method includes: (i) obtaining a plurality of 2D and/or 3D images of a patient's breast; (ii) generating a synthesized 2D image of the patient's breast from the obtained 2D and/or 3D images of the plurality; (iii) displaying the synthesized 2D image; (iv) receiving a user command, or otherwise detecting through a user interface, a user selection or other indication of an object or region in the synthesized 2D image; and (v) displaying at least a portion of one or more images from the plurality, including a source image and/or most similar representation of the user selected or indicated object or region.

Additionally and/or alternatively, the system may be configured for, and the method may include, concurrently displaying a respective source image and/or most similar representation of a tissue structure or region that corresponds to a given location of a user movable input device in the displayed synthesized 2D image. While various image processing techniques may be employed for providing the this navigational functionality, in a preferred embodiment, the system is preferably configured for, and the method further includes, generating an index map comprising identifying information of selected images of the plurality of 2D and/or 3D images that are source images or that otherwise contain a most similar representation of regions and/or objects displayed in the synthesized 2D image. The index map can thereafter be used by the system for to greatly reduce the time needed to navigate through the images, e.g., a tomosynthesis volume stack of the breast image volume.

The plurality of source images may include one or more of tomosynthesis projection images, reconstructed tomosynthesis slices, mammograms, contrast enhanced mammograms, and synthesized two dimensional images. In various embodiments, the plurality of 2D and/or 3D images of a patient's breast are acquired or synthesized X,Y coordinate slices at differing z axis locations of the breast, the images having one or more corresponding X,Y coordinate locations. In one embodiment, generating the synthesized 2D image includes constructing a merged image by importing one or more objects and/or regions from the images of the plurality into the merged image, wherein an image from which an object or region is imported into the merged image comprises a source image for that object or region. In such embodiment, objects or regions are preferably imported into the merged image at X,Y coordinate locations corresponding to the X,Y coordinate locations of the respective objects or regions in their source image. Further to such embodiment, each image of the plurality of 2D and/or 3D images preferably contains one or more regions defined by their X,Y coordinate locations that are common for all images of the plurality, wherein one of each said common region is imported from the plurality of images into the merged image based upon a comparison of one or more system and/or user defined attributes of the respective common region of each image.

In a preferred variation of this embodiment, an identified object or region of interest in a given image has priority for importation into the merged image over any other identified objects or regions of interest having the same or overlapping X,Y coordinate locations in other image slices based upon a predefined priority scheme, e.g., to reflect the relative clinical importance of the various possible tissue structures. The preferred attributes may include attributes indicative of regions of interest, such as cancers, or alternatively such as more accurate representation of breast density or breast anatomy, i.e., truthful breast-border/nipple appearance, or presence of a contrast agent in the case of contrast enhanced mammography. In general, any attribute capable to delivering a high/better-quality image can be relevant.

In various embodiments, an object or region may be automatically highlighted in the synthesized 2D image and/or displayed at least portion of the one or more images from the plurality. Additionally and/or alternatively, an object or region in the synthesized 2D image and/or displayed at least portion of the one or more images from the plurality may be highlighted in response to a further received user command or to certain user activity detected through the user interface. By way of non-limiting example, an object or region may is highlighted by a contour line representing a boundary of the highlighted object or region. Preferably, the object or region is highlighted in a manner indicating that the highlighted object or region is or contains a specified type of tissue structure.

According to another aspect of the inventions disclosed and described herein, a system and method for processing, displaying and navigating breast tissue information is provided, wherein the system is configured for, and the method includes: (i) obtaining a plurality of tomosynthesis images comprising volumetric image data of a patient's breast; (ii) generating a synthesized 2D image of the patient's breast at least in part from the tomosynthesis images; (iii) displaying the synthesized 2D image; (iv) receiving a user command, or otherwise detecting through a user interface, a user selection or other indication of an object or region in the synthesized 2D image; and (v) displaying at least a portion of one or more tomosynthesis images from the plurality, including a source image and/or most similar representation of the user selected or indicated object or region. Again, while various image processing techniques may be employed for providing the this navigational functionality, in a preferred embodiment, the system is preferably configured for, and the method further includes, generating an index map that includes identifying information of selected tomosynthesis images of the plurality that are source images or that otherwise contain a most similar representation of regions and/or objects in the synthesized 2D image.

These and other aspects and embodiments of the disclosed inventions are described in more detail below, in conjunction with the accompanying figures.

DETAILED DESCRIPTION OF THE ILLUSTRATED EMBODIMENTS

Figure 1:
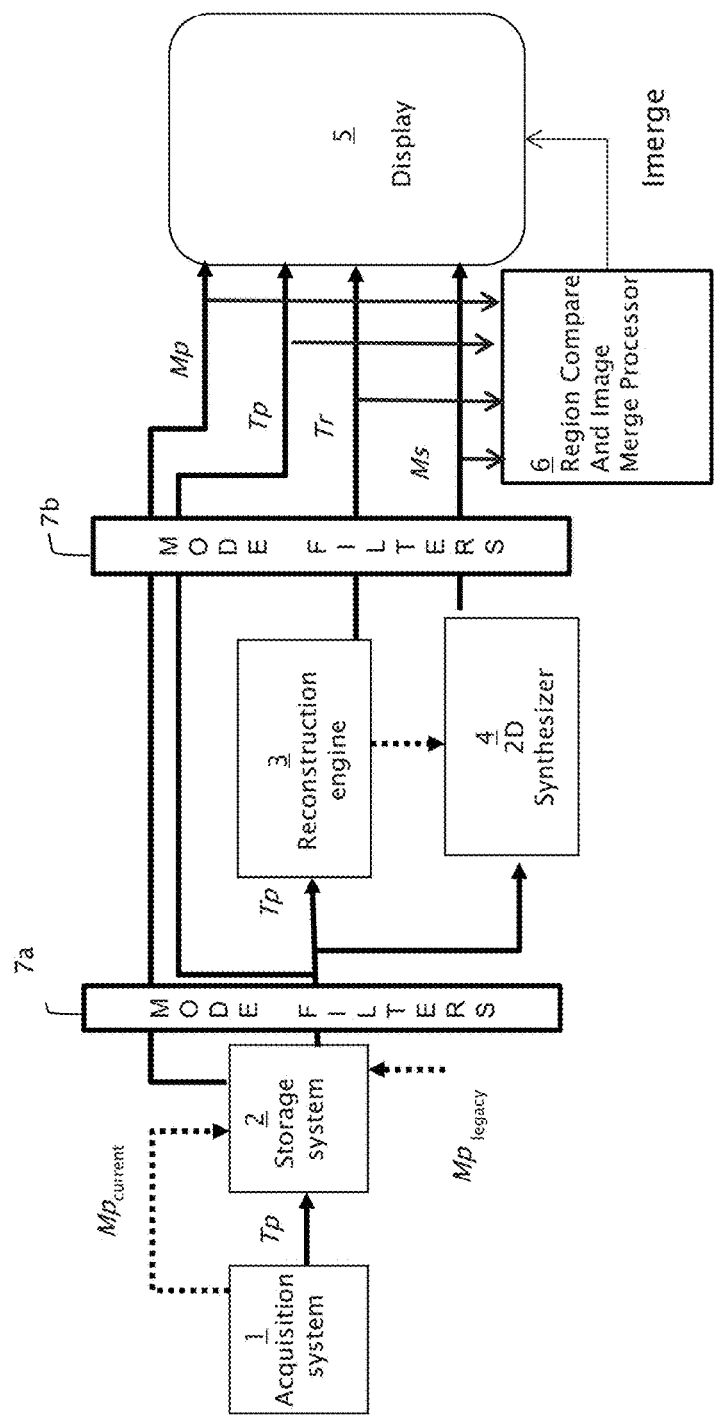
FIG. 1 is a block diagram illustrating the flow of data through a system that includes a combination mammography/tomosynthesis acquisition system and/or a tomosynthesis-only acquisition system to acquire tomosynthesis and/or mammography (including contrast mammography) images of a patient's breast, and further includes one or more processors that implement the image merge technology of the presently disclosed inventions for providing a two dimensional synthesized image by importing the most relevant data from the acquired 2D and/or 3D source images into a single merged 2D image for display to a medical professional.

In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

The following abbreviations shall have the following definitions throughout this patent specification:

Mp refers to a conventional mammogram or contrast enhanced mammogram, which are two-dimensional (2D) projection images of a breast, and encompasses both a digital image as acquired by a flat panel detector or another imaging device, and the image after conventional processing to prepare it for display and/or storage or other use.

Tp refers to an image that is similarly two-dimensional (2D), but is acquired at a respective tomosynthesis angle between the breast and the origin of the imaging x rays (typically the focal spot of an x-ray tube), and encompasses the image as acquired, as well as the image data after being processed for display and/or storage or other use.

Tr refers to an image that is reconstructed from tomosynthesis projection images Tp, for example, in the manner described in one or more of U.S. Patent Application Publication No. 2010/0135558, and U.S. Pat. Nos. 7,760,924, 7,606,801, and 7,577,282, the disclosures of which are fully incorporated by reference herein in their entirety, wherein a Tr image represents a slice of the breast as it would appear in a projection x ray image of that slice at any desired angle, not only at an angle used for acquiring Tp or Mp images.

Ms refers to synthesized 2D images, which simulate mammography images, such as a craniocaudal (CC) or mediolateral oblique (MLO) images, and are constructed using tomosynthesis projection images Tp, tomosynthesis reconstructed images Tr, or a combination thereof. Examples of methods that may be used to generate Ms images are described in the above-incorporated U.S. Patent Application Publication No. 2010/0135558, and U.S. Pat. No. 7,760,924.

$I_{MERGE}$ refers to a 2D image constructed by importing into a single image one or more objects and/or regions from any two or more of Mp, Ms, Tp or Tr images of a patient's breast, wherein an image from which an object or region is imported into the merged image comprises a source image for that object or region, and wherein objects or regions are imported into the merged image at X,Y coordinate locations corresponding to the X,Y coordinate locations of the objects or regions in their respective source image The terms $I_{MERGE}$, Tp, Tr, Ms and Mp each encompasses information, in whatever form, that is sufficient to describe the respective image for display, further processing, or storage. The respective $I_{MERGE}$, Mp, Ms. Tp and Tr images are typically provided in digital form prior to being displayed, with each image being defined by information that identifies the properties of each pixel in a two-dimensional array of pixels. The pixel values typically relate to respective measured, estimated, or computed responses to x rays of corresponding volumes in the breast, i.e., voxels or columns of tissue. In a preferred embodiment, the geometry of the tomosynthesis images (Tr and Tp), mammography images (Ms and Mp) and the merged image $I_{MERGE}$ are matched to a common coordinate system, as described in U.S. Pat. No. 7,702,142, the disclosure of which is hereby incorporated by reference in its entirety. Unless otherwise specified, such coordinate system matching is assumed to be implemented with respect to the embodiments described in the ensuing detailed description of this patent specification.

FIG. 1 illustrates the flow of data in an exemplary image generation and display system, which incorporates the merged image generation and display technology and features of the presently disclosed inventions. It should be understood that, while FIG. 1 illustrates a particular embodiment of a flow diagram with certain processes taking place in a particular serial order or in parallel, various other embodiments of the presently disclosed inventions are not limited to the performance of the image processing steps in any particular order, unless so specified.

More particularly, the image generation and display system includes an image acquisition system 1 that acquires tomosynthesis image data for generating Tp images of a patient's breasts, using the respective three dimensional and/or tomosynthesis acquisition methods of any of the currently available systems. If the acquisition system is a combined tomosynthesis/mammography system, Mp images may also be generated. Some dedicated tomosynthesis systems or combined tomosynthesis/mammography systems may be adapted to accept and store legacy mammogram images, (indicated by a dashed line and legend $Mp_{legacy}$ in FIG. 1) in a storage device 2, which is preferably a DICOM-compliant Picture Archiving and Communication System (PACS) storage device. Following acquisition, the tomosynthesis projection images Tp may also be transmitted to the storage device 2 (as shown in FIG. 1).

The Tp images are transmitted from either the acquisition system 1, or from the storage device 2, or both, to a computer system configured as a reconstruction engine 3 that reconstructs the Tp images into reconstructed image "slabs" Tr, representing breast slices of selected thickness and at selected orientations, as disclosed in the above-incorporated patents and application publication. The imaging and display system 1 further includes a 2D synthesizer that operates substantially in parallel with the reconstruction engine for generating 2D images that simulate mammograms taken at any orientation (e.g., CC or MLO) using a combination of one or more Tp and/or Tr images. The synthesized 2D images may be generated dynamically prior to display (as shown in FIG. 1) or may be stored in storage system 2 for later use. The synthesized 2D images are interchangeably referenced as T2d and Ms. The reconstruction engine 3 and 2D synthesizer are preferably connected to a display system 5 via a fast transmission link. The originally acquired Mp and/or Tp images may also be forwarded to the display system 5 for concurrent or toggled viewing with the respective Tr and/or Ms images by a medical professional.

Mode filters 7a, 7b are disposed between image acquisition and image display. Each of the filters 7a and 7b may additionally include customized filters for each type of image (i.e., Tp, Mp, Tr) arranged to identify and highlight certain aspects of the respective image types. In this manner, each imaging mode can be tuned or configured in an optimal way for a specific purpose. The tuning or configuration may be automatic, based on the type of the image, or may be defined by manual input, for example through a user interface coupled to a display. In the illustrated embodiment of FIG. 1, the filters 7a and 7b are selected to highlight particular characteristics of the images that are best displayed in the respective imaging mode, for example, geared towards highlighting masses or calcifications, or for making the merged image (described below) appear to be a particular image type, such as a 3D reconstructed slice, or a 2D mammogram.

According to one aspect of the disclosed inventions, and as described in greater detail herein, the system 1 includes an image merge processor 6 that merges relevant image data obtained from a set of available source and synthesized images of a patient's breast to provide a merged 2D image $I_{MERGE}$ for display. The set of available images used to generate the merged image $I_{MERGE}$ may include filtered and/or unfiltered Ms, Mp, Tr and/or Tp images. While FIG. 1 depicts all these types of images being input into the image merge processor 6, it is also envisioned within the scope of the disclosed inventions that the merged image may be manually configurable. For example, a user interface or preset configuration may be provided and configured to allow a user to select a particular group of two or more images or image types for generating a synthesized 2D image $I_{MERGE}$ for display.

By way of illustration, a medical professional, such as a radiologist, may wish to merge two or more reconstructed tomosynthesis slices (or slabs) in order to provide a merged image showing the most readily discerned structures in the collective tomosynthesis image data in a displayed synthesized 2D image, which essentially maps the tomosynthesis slices (or slabs) at a pixel wise granularity. Additionally or alternatively, the radiologist may combine a 2D mammogram image, whether Mp or Ms, with a 3D projection, or with selected reconstructed images, in order to obtain a customized merged image that highlights both calcifications and various tissue structures in the breast. Filters applied to each type of image can further highlight the types of structures or features in the merged image that are generally most prevalent or most readily discerned in the respective source image type. Thus, one type of filter may be applied to mammography images to highlight calcifications, while a different filter may be applied to tomosynthesis slices to highlight masses, allowing both the highlighted calcifications and highlighted tissue masses to be displayed in the single merged image. Filters may also provide the merged image with a desired look and feel; i.e., to make the merged image appear more like a tomosynthesis or mammography image.

The display system 5 may be part of a standard acquisition workstation (e.g., of acquisition system 1), or of a standard (multi-display) review station that is physically remote from the acquisition system 1. In some embodiments, a display connected via a communication network may be used, for example, a display of a personal computer or of a so-called tablet, smart phone or other hand-held device. In any event, the display 5 of the system is preferably able to display $I_{MERGE}$, Ms, Mp and Tr (and/or Tp) images concurrently, e.g., in separate side-by-side monitors of a review workstation, although the invention may still be implemented with a single display monitor, by toggling between images.

To facilitate the detection/diagnosis process, Tr slices are preferably reconstructed all to the same size for display, which can be the same as the size of an Mp or Ms image of the breast, or they can be initially reconstructed to sizes determined by the fan shape of the x ray beam used in the acquisition, and then later converted to that same size by appropriate interpolation and/or extrapolation. In this manner, images of different types and from different sources can be displayed in desirable size and resolution. For example, an image can be displayed in (1) Fit To View Port mode, in which the size of the displayed image size is maximized such that the entire imaged breast tissue is visible, (2) True Size mode, in which a display pixel on the screen corresponds to a pixel of the image, or (3) Right Size mode, in which the size of a displayed image is adjusted so that it matches that of another image being concurrently displayed, or with which the displayed image is, or can be, toggled.

For example, if two images of the same breast are taken and are not the same size, or do not have the same resolution, provisions may be made to automatically or user-selectively increase or reduce the magnification (i.e., "zoom in" or "zoom out") of one or both images, such that they appear to be the same size when they are concurrently displayed, or as a user toggles between the images. Known interpolation, extrapolation and/or weighting techniques can be used to accomplish the re-sizing process, and known image processing technology can also be used to make other characteristics of the displayed images similar in a way that facilitates detection/diagnosis. When viewing such resized images, according to one embodiment of the disclosed inventions, the merged image $I_{MERGE}$ is automatically resized, accordingly.

Thus, the system 1, which is described as for purposes of illustration and not limitation in this patent specification, is capable of receiving and displaying selectively tomosynthesis projection images Tp, tomosynthesis reconstruction images Tr, a synthesized mammogram image Ms, and/or mammogram (including contrast mammogram) images Mp, or any one or sub combination of these image types. The system 1 employs software to convert (i.e., reconstruct) tomosynthesis images Tp into images Tr, software for synthesizing mammogram images Ms, and software for merging a set of images to provide a merged image that displays, for every region of the merged image, the most relevant feature in that region among all images in the source image set. For the purpose of this patent specification, an object of interest or feature in a source image may be considered a 'most relevant' feature for inclusion in the merged image based upon the application of one or more CAD algorithms to the collective source images, wherein the CAD algorithms assign numerical values, weights or thresholds, to pixels or regions of the respective source images based upon identified/detected objects and features of interest within the respective region or between features or, in instances when the merged image is generated directly from the synthesized image without CAD assistance, simply the pixel value, weight or other threshold associated with a pixel or region of the image. The objects and features of interest may include, for example, spiculated lesions, calcifications, and the like. Various systems and methods are currently well known for computerized detection of abnormalities in radiographic images, such as those disclosed by Giger et al. in RadioGraphics, May 1993, pp. 647-656; Giger et al. in Proceedings of SPIE, Vol. 1445 (1991), pp. 101-103; U.S. Pat. Nos. 4,907,156, 5,133,020, 5,343,390, and 5,491,627, each of which being hereby incorporated by reference in its entirety.

Figure 2:
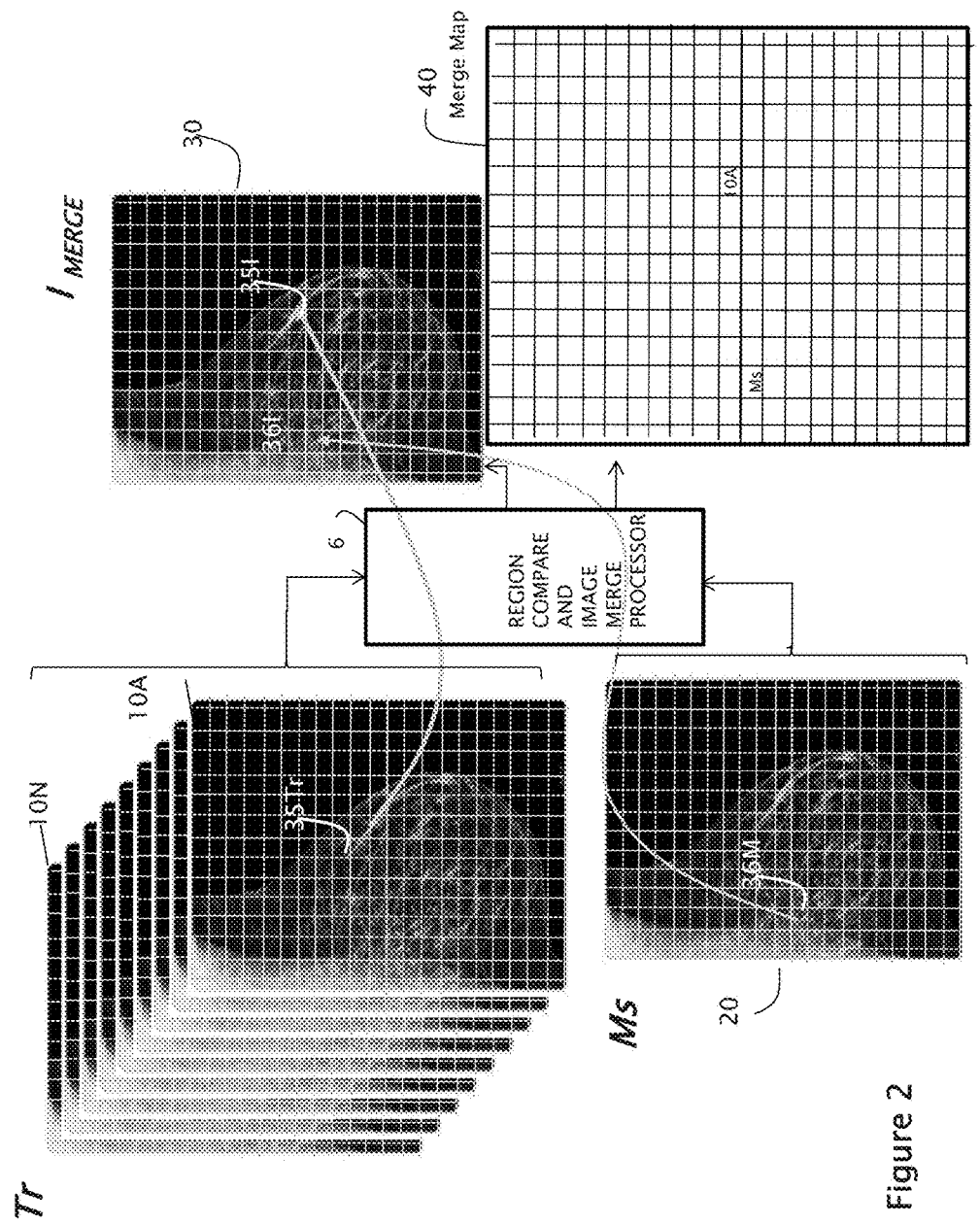
FIG. 2 is a diagram illustrating the data flow of a series of tomosynthesis slices and a synthesized 2D mammogram through the image merge technology of the presently disclosed inventions to generate a merged image and a corresponding merge (or "guidance") map.

FIG. 2 is a diagram which pictorially illustrates the merging of image data from a tomosynthesis reconstruction image data set Tr, comprising tomosynthesis slices 10A to 10N, with image data from a mammogram 20, in this case a synthesized mammogram Ms. For ease of description, filters are not shown in this example. The tomosynthesis image data set Tr and synthesized mammogram Ms are forwarded to the region compare and image merge processor 6, which evaluates each of the source images for which a merged image is to be generated (i.e., whether automatically, or based on a specific user commend) in order to (1) identify the objects and features of interest in each image for those that may be considered a 'most relevant' feature for possible inclusion in the merged image based upon the application of one or more CAD algorithms (as described above), (2)

identifies respective pixel regions in the images that contain the identified features, and (3) thereafter compares the images on a region by region basis, searching for that image with the most desirable display data for each respective region.

Figure 3:
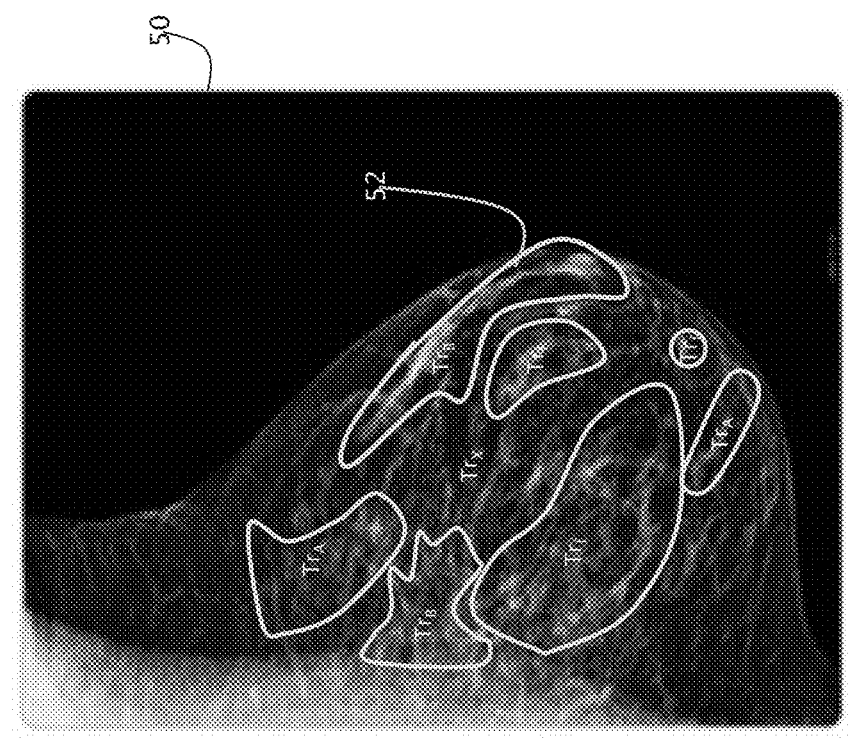
FIG. 3 depicts one embodiment of a displayed merged image, wherein certain region boundaries are dynamically identified during merge image build.

As discussed above, the image with the most desirable display data may be an image with a highest pixel value, a lowest pixel value, or which has been assigned a threshold value or weight based on the application of a CAD algorithm to the image. When the image with the most desirable display data for that region is identified, the pixels of that region are copied over to the corresponding region of the merged image. For example, as shown in FIG. 2, region 36M from image Ms is written to region 36I. Region 35 of tomosynthesis slice 10A is copied to region 35I of the merged image. Although the regions of FIG. 2 are shown as pre-defined grid regions, it is not necessary that regions be pre-defined in this manner. Rather, according to one aspect of the disclosed inventions, the boundaries of the regions may be dynamically identified during the region compare and image generation process by performing comparisons at pixel or multi-pixel granularities. By way of illustration, FIG. 3 illustrates a merged image 50, which has been constructed via the combinations of numerous regions of different source images, at arbitrary region boundaries, for example, which may be identified according to the detection of particular features within the respective source images.

Figure 4:
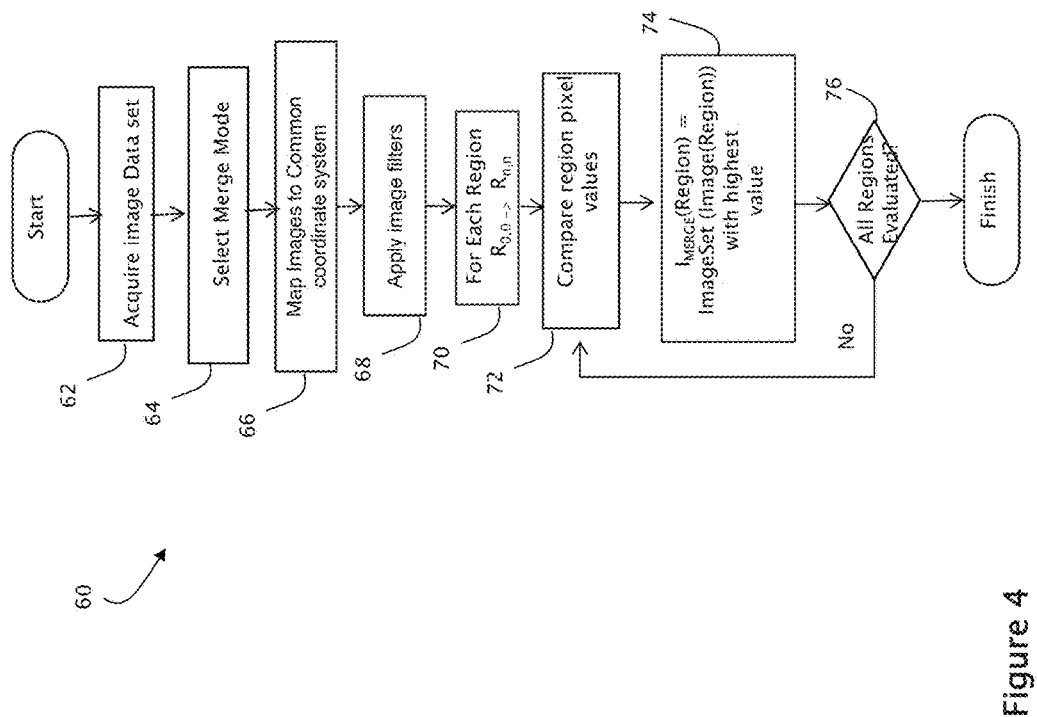
FIG. 4 is a flow diagram illustrating exemplary steps performed during an image merge process according to one embodiment of the presently disclosed inventions.

FIG. 4 is a flow diagram provided to illustrate exemplary steps that may be performed in an image merge process carried out in accordance with one embodiment of the disclosed inventions. At step 62, an image data set is acquired. The image data set may be acquired by a tomosynthesis acquisition system, a combination tomosynthesis/mammography system, or by retrieving pre-existing image data from a storage device, whether locally or remotely located relative to an image display device. At step 64, a user may optionally select a merge mode, wherein the user may designate (1) which images are to be used for the source image set to generate the merged image, (2) whether to highlight certain features in the merged image, such as calcifications, spiculated lesions or masses, and (3) whether to display the image as a lower resolution tomosynthesis image, etc. At step 66, the images that are to be merged to generate the merged image are mapped to a common coordinate system, for example, as described in the above-incorporated U.S. Pat. No. 7,702,142. Other methods of matching images of different coordinate systems may alternatively be used. At step 72, the process of comparing regions among the different images begins. At step 74, each $I_{MERGE}$ region is populated with the pixels of the region of an image from the source image set having the most desirable pixels, value, or pattern. The process of populating regions continues until it is determined, at step 76, that all regions have been evaluated, at which point the merged image is ready for display.

Figure 5A:
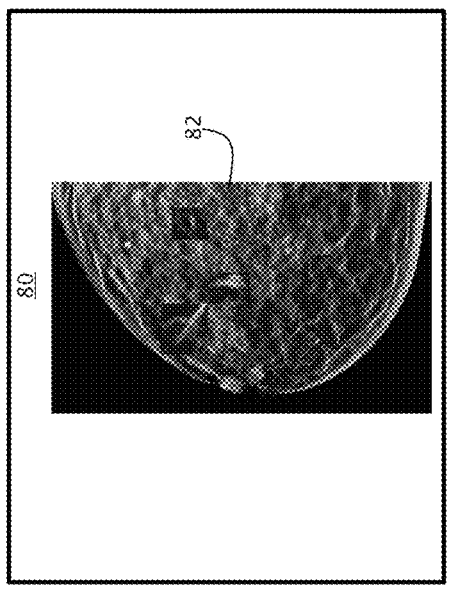
FIGS. 5A and 5B illustrate one embodiment of a display of a merged image, and a resultant display of a source image in response to selection of a region in the merged image by a user.
Figure 5B:
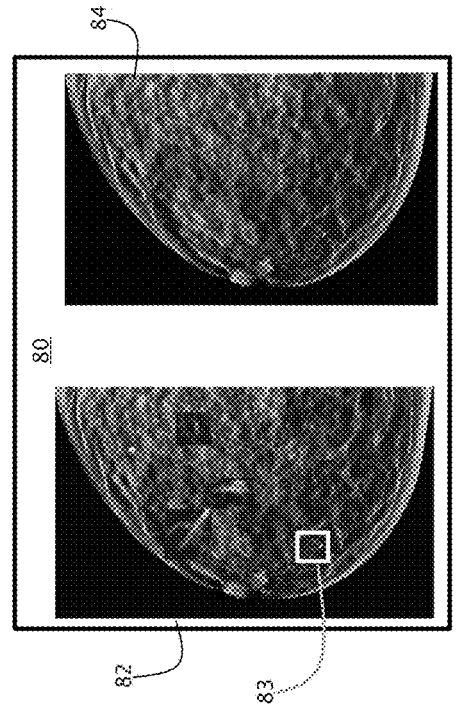

Once the merged image is generated, it may be used to assist in the navigation through a tomosynthesis image data stack from which the merge image was generated. Such navigation is a two-step process comprising selection of various objects of interest, and display of corresponding tomosynthesis images that are the source of such objects of interest in the merged image. By way of example, FIG. 5A and FIG. 5B illustrate two views of a display 80. The first view of display 80 shown in FIG. 5A illustrates a merged image 82, having regions sourced by different ones of an acquired or synthesized image set. FIG. 5B illustrates a particular feature enabled by the presently disclosed inventions, whereby a user may select a region or area 83 within the merged image 82, and the resulting image source 84 for that area is presented to the user.

The presently disclosed inventions envision many different mechanisms for selection of the objects of interest and corresponding display of the respective source images corresponding; although it is to be understood that the disclosed inventions are not limited to those described herein. For example, the selection of a region or area within the merged image may include a selection of a CAD mark, or alternatively a selection of a particular feature of interest to the reviewer. Although in both instances the most relevant slices are made available to the user, the mechanics behind the processes differ. One such preferred mechanism is illustrated in FIG. 2. As the regions of the merged image are populated, a merge (or "guidance") map 40 is also constructed. The merge map stores, for each region of the merged image, an identifier of the image from which the region is sourced. Therefore, as shown in FIG. 2, the Ms identifier is stored in region 36, while the 10A TR slice identifier is stored in region 35. As will be described in more detail herein, the merged map may be used during the display of the merged image to permit fast viewing of the respective source image(s) for user-selected regions or objects of interest.

Selection Using CAD Marks:

In addition or alternatively to use of a merge/guidance map, if the merged image is presented with a CAD overlay, the CAD overlay may include either CAD marks derived from 3D data, or CAD marks derived from 2D data (if the system has the ability to obtain 2D data). CAD marks derived from 3D data generally include, as part of the data object associated with the mark, identifiers of one or more slices which contributed to the generation of the 3D mark. When the merged image is overlaid with 3D CAD data, selection of the CAD mark results in the retrieval of the series of slices that contributed to the mark. In one embodiment, the central image slice is displayed; in alternate embodiments, the image slice having the highest weight is displayed; and in a still further alternate embodiment, the image slice having the least visual noise (i.e., the clearest image) is displayed.

Selection by Objects of Interest:

As an alternate to selecting by CAD marks, a mechanism is provided for allowing a user to select any object on a merged image, whether it is a CAD mark, or a feature of interest, such as any abnormality or irregularity in the image. In one embodiment, the user or system may select a region, using for example a mouse click for a single pixel area, or a click and drag action to select a larger region. Alternatively, the user may be provided with a selection of graphical frames of various or variable sizes, and have the ability to move the frame to different locations within the merged image to select areas when it is desired to view additional tomosynthesis image slices. In response to such a selection, the particular image slice for initial display may be selected in a variety of ways.

For example, an image slice could be selected based on the weighting of its associated pixel within the selected region. Or a particular image slice may be selected because a particular feature which is selected, or which is near a pixel or region that is selected, is best viewed in the selected image slice, e.g., provides the clearest view of that region. Thus, the identification of a particular image slice that is most relevant to a selected pixel or region may utilize pixel information that surrounds the selected object, for example, using region growing techniques known to those in the art. Thus, pixels that neighbor the selected pixel or region are included in the evaluation for relevant slices if the pixels have a characteristic that satisfies a certain threshold established by the user; for example, including but not limited to the pixels having a particular weight, or being arranged in a particular pattern, etc.

Alternatively, a group of image slices may be selected, e.g., a successive order of image slices, with a central slice or most heavily weighted slice being first presented. As described above, alternatively the image slice within the group having the least noise, i.e., the clearest slice, may be provided. In addition, the selection of an image slice for presentation may also take into account a desired visualization mode. Thus, if the user-specified purpose is to visualize calcifications, an image slice having calcification features may be presented ahead of another slice within the group having a lesser calcification characteristic.

It will be appreciated that the disclosed and described systems and methods in this patent specification are designed to condense the image information made available from a tomosynthesis reconstruction volume (or "stack") containing a patient's 3D breast image data down to a single, synthesized 2D image, similar to a conventional 2D mammographic image. By reviewing this synthesized 2D image concurrently with the 3D tomosynthesis stack, it is possible to provide a much more efficient and accurate review of the patient's breast tissue. This is because the synthesized 2D merged image can act as a guidance-map, so that the medical professional reviewing the images can focus on the synthesized 2D image for detecting any objects or regions of interest that merit further review, and the system can provide immediate, automated navigation to a "best" corresponding tomosynthesis image slice (or a subset of adjacent tomosynthesis slices) to allow the medical professional to conduct this further review, verify and evaluate the finding. Thus, it is preferred, although not required for practicing all embodiments of the disclosed inventions, for the medical professional to employ a user interface that can display a respective synthesized 2D merged image along-side the tomosynthesis volume image slices, for concurrent viewing of both.

Figure 6:
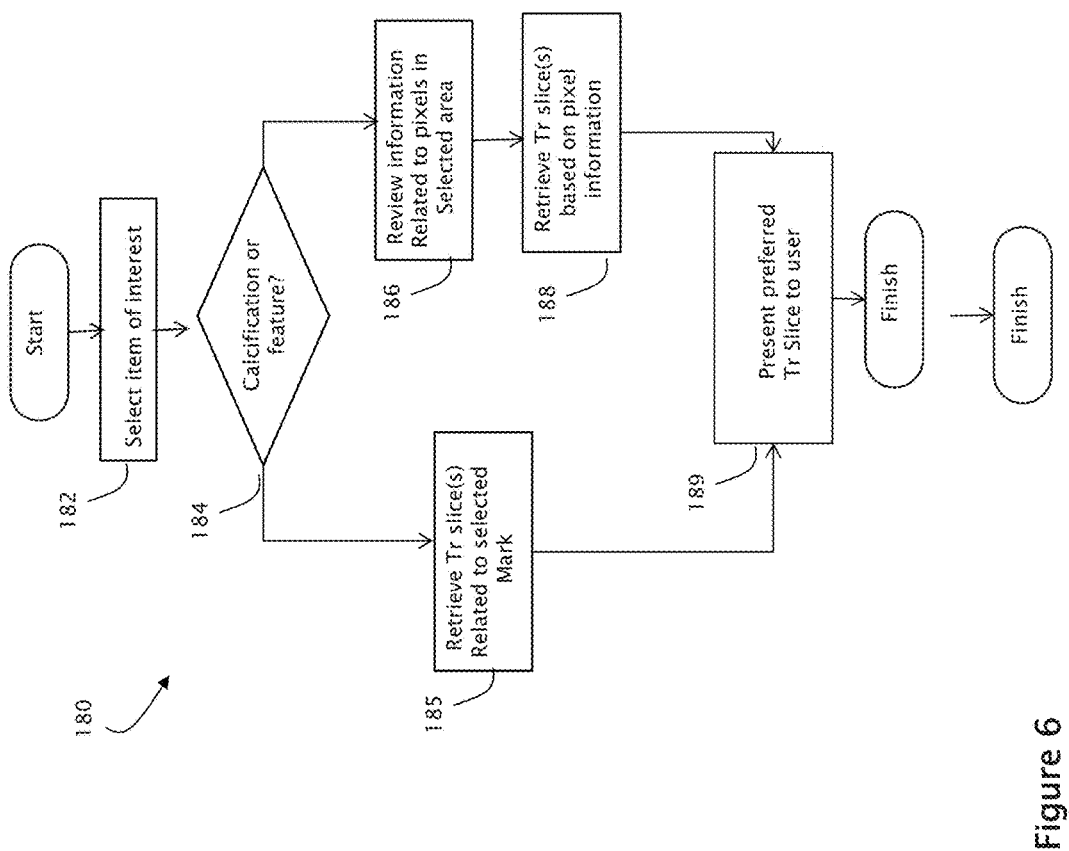
FIG. 6 is a flow diagram illustrating an exemplary process for retrieving and presenting a reconstructed tomosynthesis image slice in response to user-selection of an object of interest in a synthesized 2D image, according to one embodiment of the presently disclosed inventions.

FIG. 6 illustrates one exemplary process 180 for retrieving and presenting a Tr image slice in response to user-selection of an object of interest in a merged image, which may be implemented using a software program according to one embodiment of the presently disclosed inventions. The process 180 operates, in response to a selection of an object of interest in a merged image at step 182. At step 184, the process determines whether the selected object is a CAD mark or a non-CAD mark feature of interest. If it is a CAD mark, at step 185, the Tr slices related to the CAD mark are retrieved. At step 189, one of the Tr slices is selected and presented for display based on at least one of its relative position in the stack, relative weight of the voxel value of the slice, a selected visualization mode, etc. If, at step 184, the process determines that the selected object was a non-CAD mark feature of interest, then at step 186, the source Tr images associated with the selected region are evaluated, and a particular Tr source is selected for display based on its relative voxel value as compared to voxel values in other Tr sources that map to the region. It is noted that the Tr sources that contribute to pixel values within a selected region may be intermittently spaced within the 3D tomosynthesis volume. Thus, when the most relevant Tr source image is selected, it may be presented either alone, or as part of a stack of images together with one or more neighboring Tr slice images. The most relevant Tr source may be the presented image, or alternatively another image in the stack associated with the most relevant image may be first presented, for example if that particular image is clearer.

Figure 7:
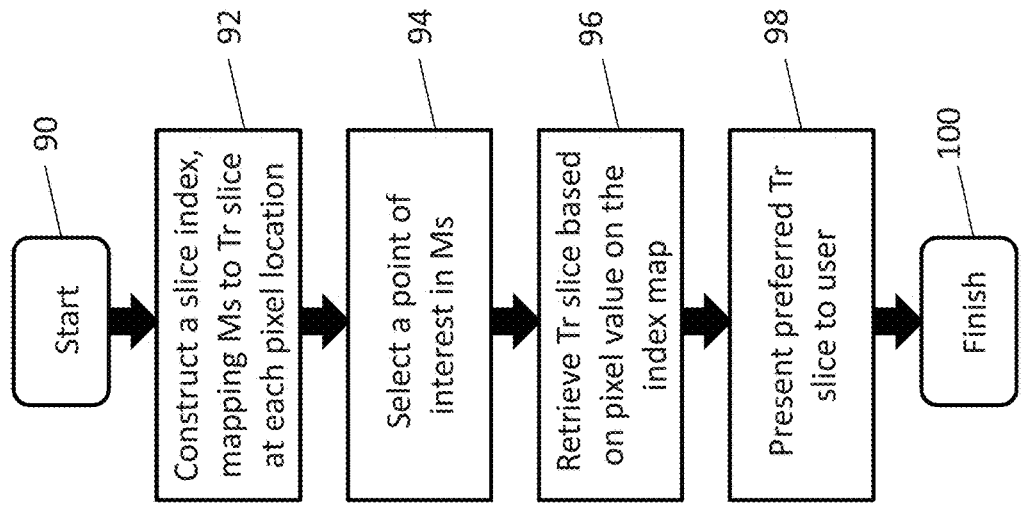
FIG. 7 is a flow diagram illustrating another exemplary process for retrieving and presenting a reconstructed tomosynthesis image slice in response to user-selection of an object of interest in a synthesized 2D image, according to another embodiment of the presently disclosed inventions.

FIG. 7 depicts another process that may be software-implemented for using a synthesized 2D image for navigating a 3D tomosynthesis image stack ("tomosynthesis stack"), according to another embodiment of the presently disclosed inventions. At initiation or activation 90, the process includes, at step 92, constructing a tomosynthesis image slice index map, wherein the pixel locations of the synthesized 2D image are mapped to corresponding pixel locations in pertinent image slices of the tomosynthesis stack. In particular, the tomosynthesis stack index map includes identifying information of selected tomosynthesis slice images from the breast volume stack that are source images or that otherwise contain a most similar representation of regions and/or objects displayed in the synthesized 2D image. The tomosynthesis stack index map is preferably generated prior to when a medical professional is ready to conduct his or her review of the breast image data. The details for constructing the tomosynthesis stack index map, in accordance with one preferred embodiment, are described below in conjunction with FIG. 8.

Figure 9:
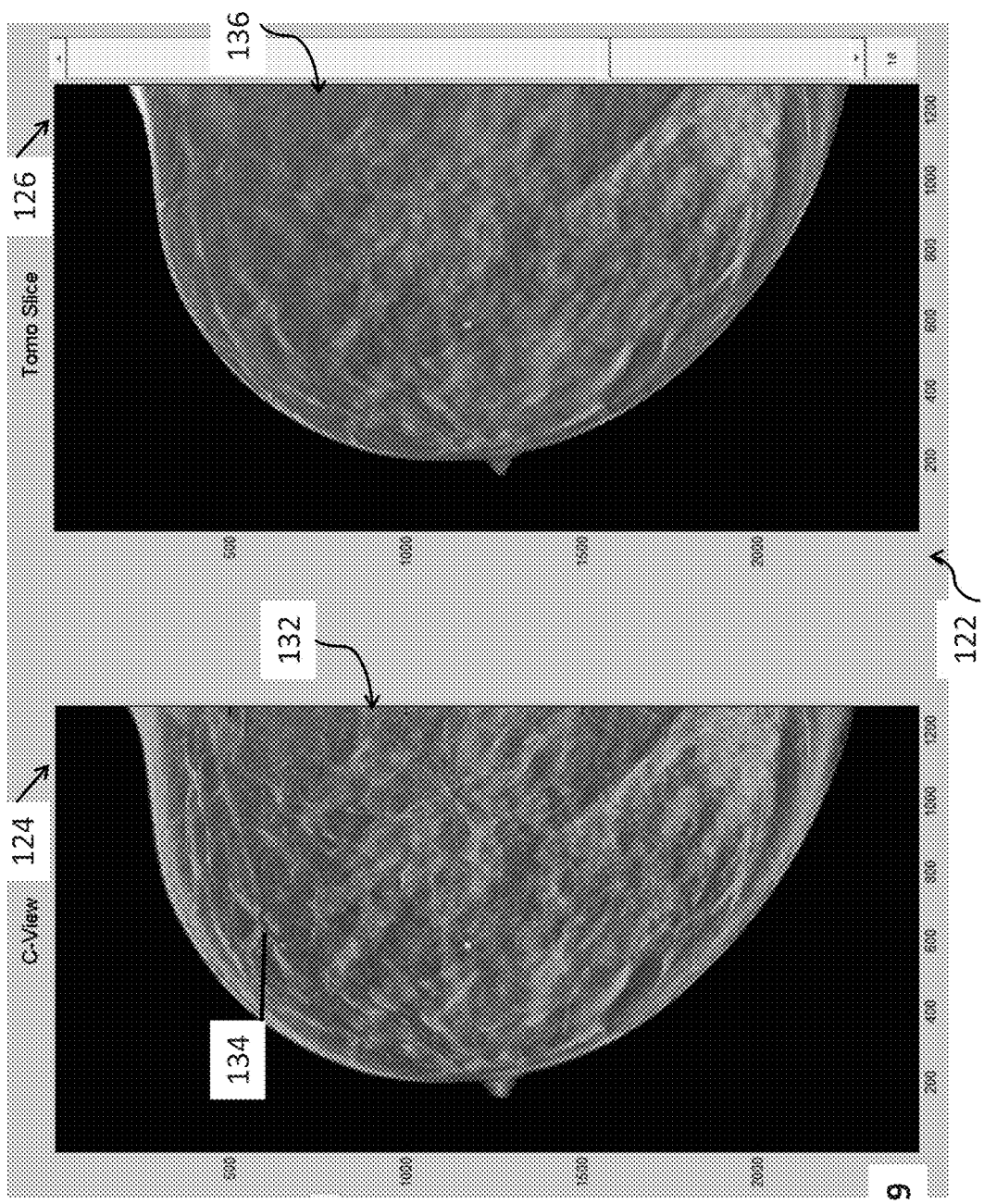
FIG. 9 depicts an exemplary user interface, including a left-hand side monitor displaying a synthesized 2D image of a patient's breast, including a highlighted tissue structure, wherein the highlighting is in the form of a contour line that represents a boundary of the highlighted tissue structure, and a right-hand side monitor displaying the tomosynthesis image from which the highlighted tissue structure was imported into the 2D image, or which otherwise provides a best view of the highlighted tissue structure.
Figure 10:
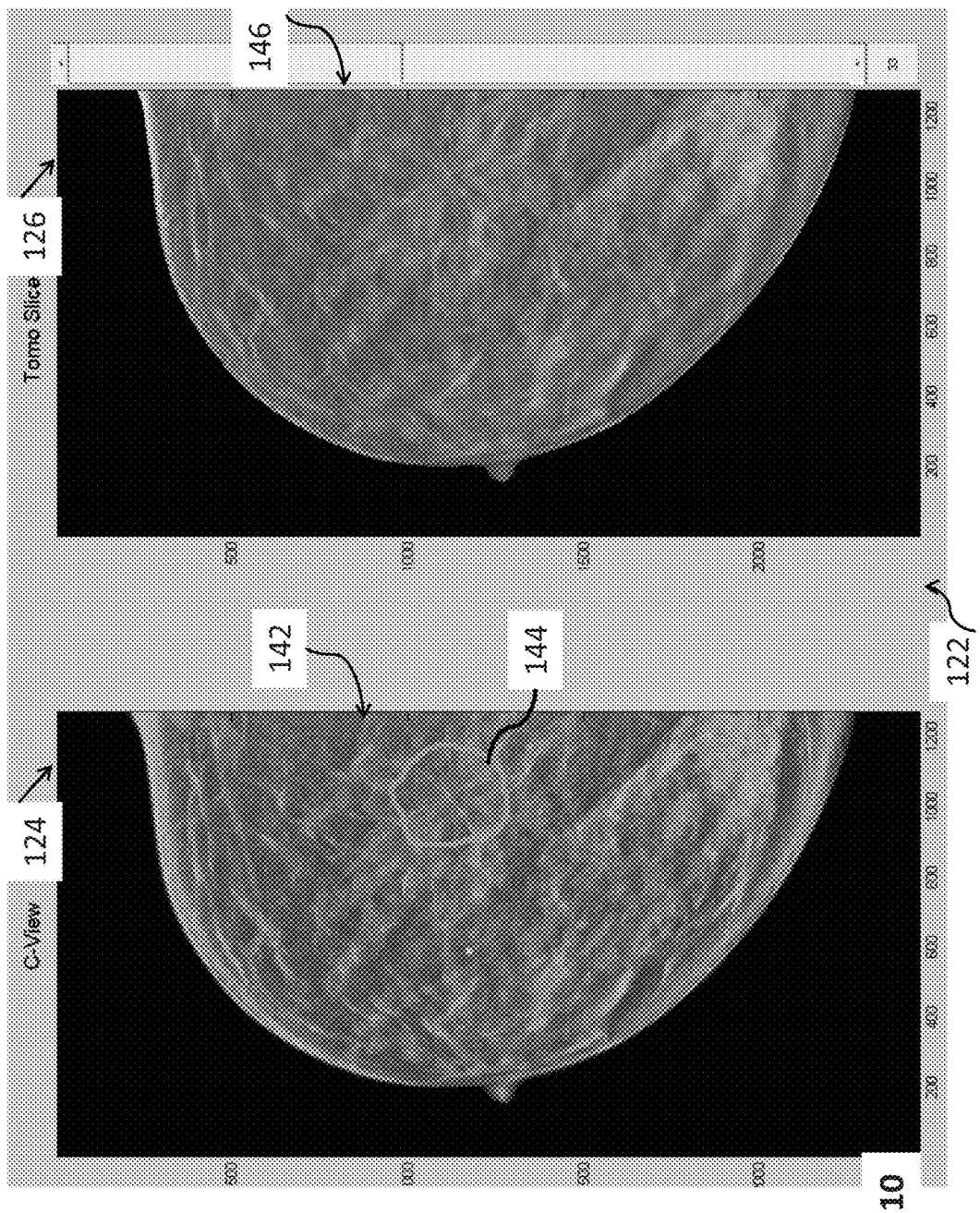
FIG. 10 depicts the user interface of FIG. 9, again displaying a synthesized 2D image of a patient's breast including a highlighted spiculated mass in the left-hand monitor, and a right-hand side monitor displaying the tomosynthesis image from which the depicted spiculated mass was imported into the 2D image, or which otherwise provides a best view of the spiculated mass.
Figure 11:
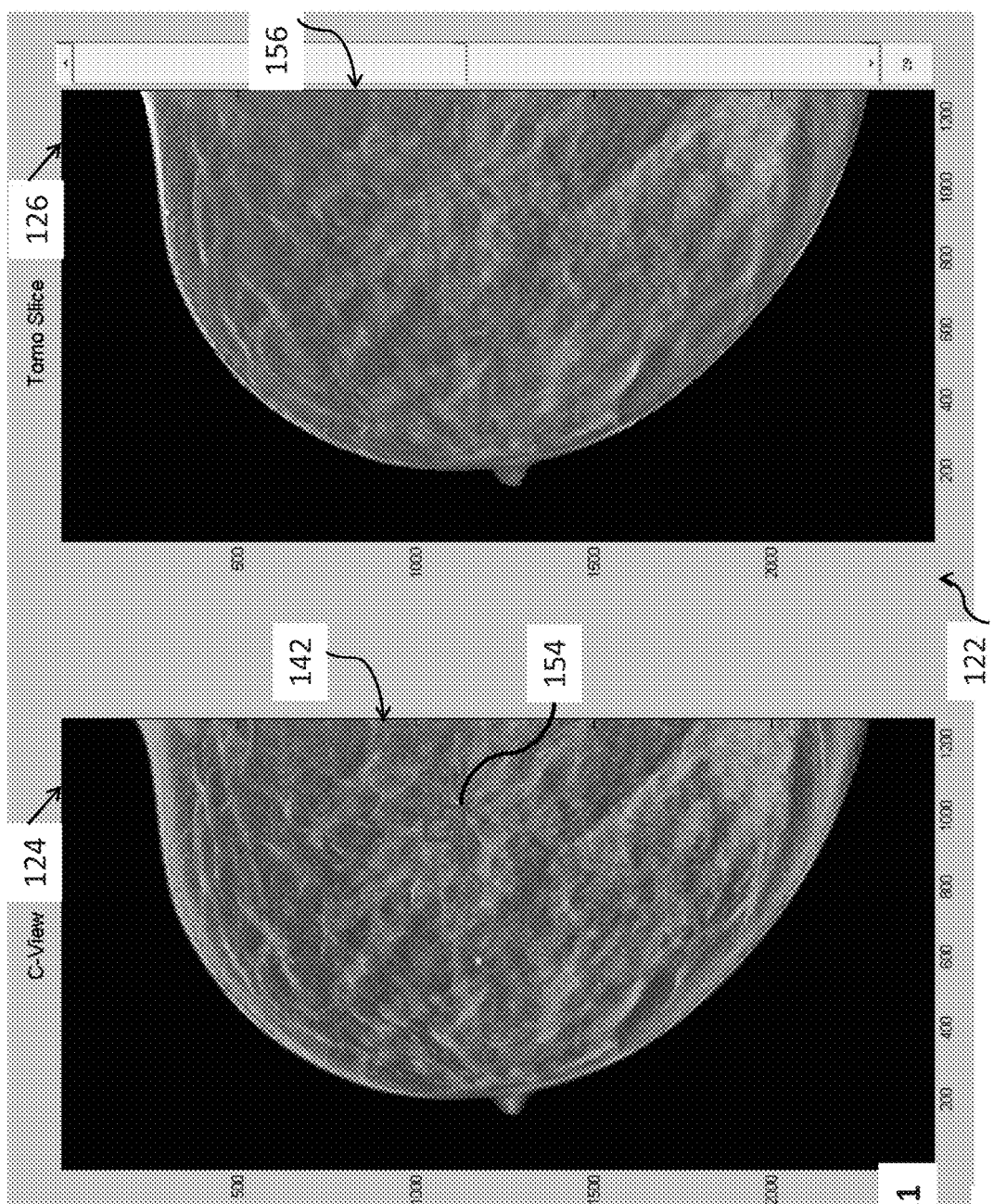
FIG. 11 depicts the user interface of FIG. 10, including the same breast image displayed in the left-hand side monitor, but now highlighting a region containing micro-calcifications, with the right-hand side monitor displaying the tomosynthesis image from which the highlighted region containing the micro-calcifications was imported into the 2D image, or which otherwise provides a best view of the micro-calcifications.

The synthesized 2D image is displayed to the medical professional (interchangeably referred to as the "user" of the described system), typically on a workstation having side-by-side monitors as depicted in FIGS. 9-11. Depending on how the user has configured the workstation, when initiating review of particular patient breast image data, only the synthesized 2D image may be presented, e.g., on the left-hand-side monitor, with the right-hand-side monitor being blank, or perhaps depicting a first or middle image slice from the tomosynthesis stack, preferably depending on a user-selectable configuration. In one embodiment, the system will initially display the synthesized 2D image on the left-hand-side monitor, and a "most relevant" one of the tomosynthesis slice images on the right-hand-side monitor, which was determined by the system based upon the displayed tomosynthesis slice being most similar in appearance to the synthesized 2D image, or having the relatively most interesting objects, out of the tomosynthesis image stack for the entire breast volume.

Thereafter, the medical professional (user) may use the user-interface to activate the navigational capability of the system. In particular, at step 94, the user may affirmatively input a command to select a particular object or region in the displayed synthesized 2D image. Alternatively, the system may be configured sot that the user merely positions a "pointer," e.g., a movable cross or arrowhead that is controlled using a mouse or similar input device), overlying an object or region in the displayed synthesized 2D image, thereby "indicating" an interest in the item. In response to the received command or indication, using the index map, the system may easily retrieve, at step 96, and display on the right-hand-side monitor, at step 98, the tomosynthesis slice that is either the direct source of the user selected/indicated object or region, or which otherwise contains a most similar representation of the object or region as depicted in the displayed 2D image. Additionally and/or alternatively, the system may be configured for concurrently displaying a respective source image and/or most similar representation of a tissue structure or region that corresponds to a given location of a user movable input device in the displayed synthesized 2D image.

The plurality of 2D and/or 3D images from which a synthesized 2D image is generated may include tomosynthesis projection images, tomosynthesis reconstruction slices, mammography images, contrast enhanced mammography images, synthesized 2D images, and combinations thereof. It will be appreciated that the synthesized 2D image advantageously incorporates the most relevant information from each of the underlying acquired and computer generated image data sets of the patient's breast. Thus, different regions of pixels in the displayed synthesized 2D image may be sourced from corresponding different images in the underlying image data set, depending on which underlying image is best for viewing an object of interest, e.g., a mass or a calcification, in the respective region. The particular regions may be identified statically, i.e., within a particular grid, or dynamically, i.e., based on identified objects of interest, and may range in granularity from as little as one pixel, to all pixels in the respective image. In one embodiment, priority is given to first importing into a merged image under construction those regions containing one or more specific tissue structures of interest in the images of a tomosynthesis image data set (or "stack"), and thereafter populating the remaining regions of the merged image with the otherwise most relevant regions from the images, as described above.

The user interface may additionally include features to enable the medical professional to manipulate the presented tomosynthesis data, for example, to allow the medical professional to scan through adjacent image slices of the tomosynthesis stack, or to further zoom (magnify) into a selected region, to place markers, or alternatively to apply filters or other image processing techniques to the image data. In this manner, the medical professional may quickly review a large stack of tomosynthesis data by utilizing a synthesized 2D image for navigation purposes, thereby increasing the performance and efficiency of breast cancer screening and diagnosis. According to a further aspect of the disclosed inventions, it has been determined or otherwise appreciated that particular types of images may include or be superior for viewing different types of relevant information. For example, calcifications are typically best visualized in 2D mammograms, while masses are typically best visualized using 3D reconstructed images.

Thus, in one embodiment of the disclosed inventions, different filters are applied to each of the different types of underlying 2D and/or 3D images in the image data set used to generate the merged image, the filters selected to highlight particular characteristics of the images that are best displayed in the respective imaging mode. Appropriate filtering of the images prior to generating the merged image helps ensure that the final merged image includes the most relevant information that can be obtained from all the underlying image types. Additionally and/or alternatively, the type of filtering performed for the various images may be defined via user input, which permits a user to select a 'merge mode', for example, geared towards highlighting masses, calcifications, or for making the merged image appear to be a particular image type, such as a 3D reconstructed slice, or a 2D mammogram.

Synthesizing the 2D image may be accomplished in a variety of ways. For example, in one embodiment, general purpose image filtering algorithms are used to identify features within each of the respective 2D and 3D images, and a user may select whether to use 2D filtered data or 3D filtered data to generate the merged image. Alternatively, 2D or 3D filtered data may be automatically selected in accordance with a particular visualization mode that has been user selected; for example, 2D filtered data may be automatically selected by the system for calcification visualization mode, while 3D filtered data may be automatically selected by the system for mass visualization modes. In one embodiment, two different merged images may be constructed, one for each mode; alternatively, a single merged image may be constructed that takes into account the respective filtered image data results from all available image types.

In one embodiment, features (representing potential objects of interest) are identified in the available source images and thereafter weighted, e.g., on a pixel by pixel or region by region basis in each respective image. A 2D image is then constructed by incorporating the respective regions having the most significant weight in individual images of the available source images. The size of the region may vary in granularity from one pixel to many (or even all) pixels of the respective image, and may be statically pre-defined, or may have margins that vary in accordance with the varying thresholds of the source images. The synthesized (aka "merged") image may be pre-processed and stored as a DICOM object following tomosynthesis acquisition, and thereafter forwarded with the reconstruction data for subsequent review by a medical professional. Such an arrangement removes the need to forward weighting information for each reconstructed slice. Alternatively, the stored DICOM object may include the weighting information, allowing the merged image to be dynamically constructed in response to a request for a synthesized 2D image at the medical professional's work station. In one embodiment, both the weighting information and the synthesized 2D image may be provided in the DICOM object, allowing presentation of a default merged image, while still enabling customization according to the personal workflow of the reviewer. To be clear, the weighting information can be stored with the image itself, and need not be a separate file.

It is realized that the visualization of the synthesized 2D images may have some drawbacks. For example, there may be neighboring regions in the merged image which exhibit bright calcifications, but which in fact are sourced from image slices that are distant from one another in the z plane. Therefore, what may appear to be a cluster of micro-calcifications in the 2D image may, in fact, be individual calcifications that are distributed (i.e., along the z-axis) throughout the breast and thus do not actually represent a micro-calcification cluster that requires further review. Thus, according to a further aspect of the disclosed inventions, a 'cluster spread indicator' may be provided with the synthesized 2D image, which visually indicates the distribution of calcifications along the z-plane, allowing the medical professional to quickly assess whether a group of calcifications comprise a calcification cluster.

In some instances, the system may determine based on the index map information that more than one tomosynthesis image slice should be displayed for a selected/indicated object type or region, for example, a spiculated mass. In such instances, a series of two or more adjacent tomosynthesis slices are displayed, one after the other, at a timing interval that is preferably user selected. As will be additionally described herein, the user may select or indicate more than one object or region in a given synthesized 2D image. Once the user has completed his or her review of the displayed tomosynthesis slice(s), the process is complete (at step 100) for the particular breast image data.

As previously pointed out, while various image processing techniques may be employed for providing the this navigational functionality, in a preferred embodiment, the system is preferably configured for, and the method further includes, generating an index map comprising identifying information of selected images of the plurality of 2D and/or 3D images that are source images or that otherwise contain a most similar representation of regions and/or objects displayed in the synthesized 2D image. The index map can thereafter be used by the system for to greatly reduce the time needed to navigate through the images, e.g., a tomosynthesis volume stack of the breast image volume.

An implementation of one preferred process 102 for generating an index map will now be described in conjunction with the flow diagram shown in FIG. 8. Two parallel processes are initially employed. In one process, the image data contained in the synthesized 2D image 104 is mapped to selected tomosynthesis image slices of a 3D volume 106 to construct a "generic" index map 108. In particular, the pixel locations in the 2D image 104 is mapped to the pixel locations in the respective 3D (tomosynthesis) images 106 based entirely on image similarity, akin to the pieces of a jigsaw puzzle. In other words, the generic index map 108 is based entirely on best-fit matching of the appearance of the data in the 2D image to the appearance of the data in the respective 3D images, wherein the slice identification and X,Y coordinates of a 3D image having a most similarly appearing pixel region to a corresponding X,Y region in the 2D region is selected. Potential importance of the respective objects and features in the synthesized 2D image is not taken into account for constructing the generic index map 108.

Figure 8:
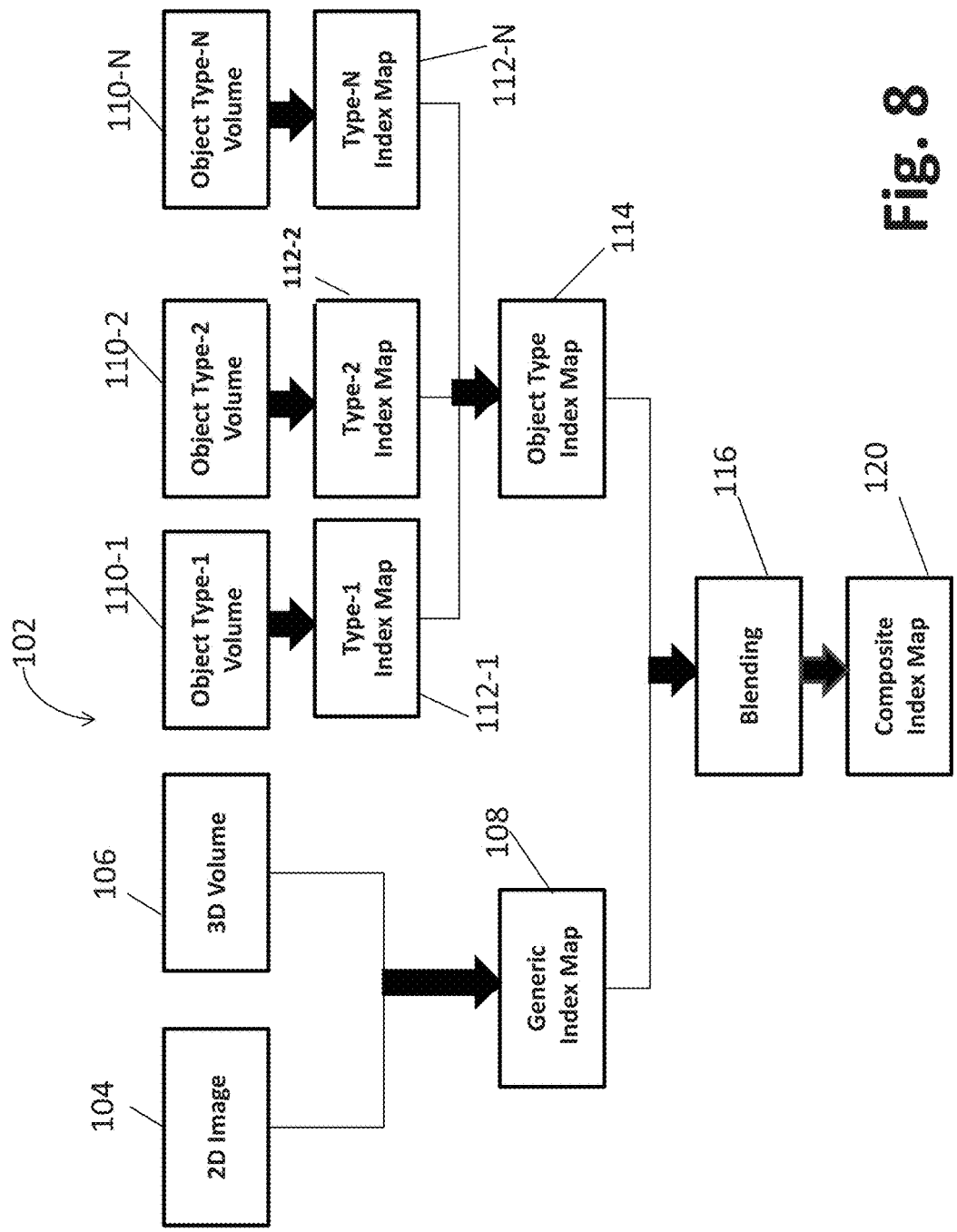
FIG. 8 is a flow diagram illustrating a process for constructing a composite index map of a synthesized 2D image to a corresponding reconstructed tomosynthesis image stack, according to still another embodiment of the presently disclosed inventions.

However, in parallel with the creation of the generic index map 108, an object type index map 114 is generated, in which individual object types, designated as 110-1 to 110-n in FIG. 8, in the synthesized 2D image are prioritized and assigned weighted values to influence the selection of the best corresponding 3D tomosynthesis image slice. In particular, an individual object type index map, designated as 112-1 to 112-n in FIG. 8, is generated for each object type identified in the synthesized 2D image, e.g., blob density, spiculated masses, micro-calcifications, etc. The individual object type index maps 112-1 to 112-n are then combined to construct the full object type index map 114, which is then blended, at step 116, with the generic index map 108 to provide a composite index map 120, wherein the object type image data is prioritized relative to the generic image data. The composite index map 120 is then used by the system for navigating the image slices of the 3D volume 106 in response to a selected or indicated location on the 2D image 104. In this manner, different object types having overlapping X,Y coordinates, i.e., due to their location at different z-axis positions in the volumetric breast image, can nevertheless be separately navigated for selective viewing, since separate mapping indexes are provided (See below example with respect to FIGS. 10 and 11).

As noted above, in various embodiments, an object or region may be automatically highlighted in the synthesized 2D image and/or displayed at least portion of the one or more images from the plurality. Additionally and/or alternatively, an object or region in the synthesized 2D image and/or displayed at least portion of the one or more images from the plurality may be highlighted in response to a further received user command or to certain user activity detected through the user interface. By way of non-limiting example, an object or region may is highlighted by a contour line representing a boundary of the highlighted object or region. Preferably, the object or region is highlighted in a manner indicating that the highlighted object or region is or contains a specified type of tissue structure.

By way of illustration, FIG. 9 depicts an exemplary work station display 122, including a left-hand side monitor 124 ("C-View") displaying a synthesized 2D image 132 of a patient's breast. The synthesized 2D image 132 includes a highlighted tissue structure 134, wherein the highlighting is in the form of a contour line that represents a boundary of the tissue structure. As noted above, this highlighting may have been done automatically by the system, e.g., at the time the 2D image 132 is initially displayed, or only in response to a specific user command or indication, e.g., by hovering a pointer over the object 134 in the 2D image 132. The work station display 122 also includes a right-hand side monitor 126 displaying the respective tomosynthesis image 136 (which is slice no. 18 of the tomosynthesis volume stack, as indicated in the lower right hand side of the monitor 126), which is the source image or which otherwise provides a most similar view of the highlighted tissue structure 134 as seen in the synthesized image 132. In particular, the user interface associated with the display 122 allows for a user to select or otherwise indicate a location on the synthesized 2D image 132, e.g., by displaying a pointer, a cross, a circle, or other similar geometrical object, and then input a certain command type (e.g., mouse click) that will be recognized by the system as a request from the user to have the corresponding source or otherwise most similar tomosynthesis slice(s) depicting the region or object underlying the pointer displayed in monitor 126.

FIG. 10 depicts the work station display 122, wherein a different synthesized 2D breast image 142 is displayed in the left-hand side C-View monitor 124. The synthesized 2D image 142 includes a highlighted tissue structure 144, wherein the highlighting is in the form of a geometric shape, in this case a circle, to indicate that the object 144 is a spiculated mass. Again, this highlighting may have been done automatically by the system, e.g., at the time the 2D image 142 is initially displayed, or only in response to a specific user command or indication, e.g., by hovering a pointer over the object 144 in the 2D image 142. The right-hand side monitor 126 is displaying the respective tomosynthesis image 146 (which is slice no. 33 of the tomosynthesis volume stack, as indicated in the lower right hand side of the monitor 126), which is the source image or which otherwise provides a most similar view of the highlighted tissue structure 144 as seen in the synthesized image 132.

It should be appreciated that there will be instances in which the mapping between an object or region in the merged 2D image to the respective object or region in the displayed (i.e., source or "best") image may not necessarily be 1-to-1, and will possibly be "1-to-many" in certain circumstances, for example, when multiple line structures on different tomosynthesis image slices combine together to form a line-crossing structures in the synthesized 2D image. By way of example, FIG. 11 depicts the user work station display 122, including the same synthesized 2D breast image 142 as displayed in FIG. 10, but now highlighting a region 154 containing micro-calcifications, with the right-hand side monitor displaying the tomosynthesis image slice 156 (which is slice no. 29 of the tomosynthesis volume stack, as indicated in the lower right hand side of the monitor 126), from which the highlighted region 154 was imported into the 2D image 142, or which otherwise provides a best view of the micro-calcifications. In particular, because the spiculated mass structure 144 and region of micro-calcifications 154 are in very close proximity in FIG. 142, a different one may be highlighted depending on a specific user command (e.g., to highlight a certain tissue type), or by slight adjustment of the position of the pointer of the user interface.

As explained above, this above described examples with respect to FIGS. 9-11 are readily accomplished by the index map constructed at the same time (or after—depending on the system implementation) the synthesized 2D image is generated. Alternatively, if no index map is available, for any given such user selected/specified point/location on the 2D image displayed in the left-hand-side monitor 124, the system may execute an algorithm to automatically compute the best corresponding image (i.e., X,Y and Z) within the tomosynthesis stack for display on the right-hand-side monitor 126. A "tomosynthesis slice indicator" may optionally be provided on the left-hand-side monitor 124, which indicates which tomosynthesis slice number (numbers) would be displayed on the right-hand-side monitor 126 based on a current location of a user curser on the 2D image. With this feature, the reviewer need not be distracted by constantly changing image displays on the right-hand-side monitor 126, while still providing the reviewer with an understanding of the z-axis location in the tomosynthesis volume stack of a particular object in the 2D image.

In accordance with a further aspect of the disclosed inventions, the available features of the user interface may be extended to function, not only based point/location of the merged image, but also based in a similar fashion on a structure/object/region. For example, particular objects or region(s) in the merged image may be automatically highlighted when displayed, based on the system recognition of possible interest in the respective objects, or of objects located in the respective region(s). In one embodiment, shown in FIG. 8, this highlighting is in the form of a contour line 108 that represents a boundary of a highlighted tissue structure. A contour line may be similarly used to highlight regions of interest in the displayed image, e.g., containing a number of calcification structures. In some embodiments, the system is configured to allow the user to "draw" a contour line on the merged image as a way of selecting or otherwise indicating an object or region of interest for causing the system to concurrently display one or more underlying source images of the selected or indicated object or region.

In preferred embodiments, the system employs known image processing techniques to identify different breast tissue structures in the various source images, and highlight them in the merged image, in particular, tissue structures comprising or related to abnormal objects, such as micro-calcification clusters, round-or-lobulated masses, spiculated masses, architectural distortions, etc.; as well as benign tissue structures comprising or related to normal breast tissues, such as linear tissues, cysts, lymph nodes, blood vessels, etc. Furthermore, an object or region consisting of or containing a first type of tissue structure may be highlighted in a first manner in the displayed merged image, and an object or region consisting or containing a second type of tissue structure may be highlighted in a second manner different from the first manner in the displayed merged image.

In various embodiments, the user may input a command through the user interface selecting or otherwise identifying a certain type of tissue structure, and, in response to the received command, the system performs one or both of (i) automatically highlighting in the displayed merged image objects comprising the selected type of tissue structure and/or regions containing one or more objects comprising the selected type of tissue structure, and (ii) automatically concurrently displaying the respective source slice (or otherwise the slice with best depiction of) a tissue structure of the selected type in the breast image data, e.g., a most prominent one of the selected tissue structure type based on a comparison, if more than one is detected in the source image stack. Thus, when the user "click" on (or very close to) a micro-calcification spot/cluster in the merged 2D image, and the system automatically concurrently displays the source (or otherwise best) tomosynthesis image slice including the corresponding micro-calcification in 3D. By way of another example, a user can select (through the user interface) a region in the 2D merged image that has the appearance with radiating line patterns (often an indication of spiculated masses), and the system will concurrently display the source (or otherwise best) 3D tomosynthesis slice, or perhaps to a series of consecutive tomosynthesis slices, for viewing the radiating line patterns.

In various embodiments, the user may input a command through the user interface, activating dynamic display functionality, wherein the system automatically highlights those objects and tissue structures that (dynamically) correspond to the location of a user movable input device in the displayed merged image. In such embodiments, the system may further comprise automatically concurrently displaying a respective source image of a highlighted selected tissue structure that corresponds to a given location of a user movable input device in the displayed merged image, again, on a dynamic basis.

In one embodiment, the system can be activated to provide a "shadow" cursor is displayed on the right-hand-side monitor 126, in a location corresponding to the same (x,y) location as the user's actual curser on the left-hand-side monitor 124, so that moving the curser around in the 2D image moves the shadow curser in the tomosynthesis image at same X,Y coordinates. The reverse can also be implemented, i.e., with the active user curser operable in the right-hand monitor 126, and the show curser in the left-hand monitor 124. In one implementation, this dynamic display feature allows the system to follow the user's point of interest, e.g. mouse cursor location, in the 2d merged image, and dynamically display/highlight the most "meaningful" region(s) underneath in real time. For example, the user can move the mouse (without clicking any button) over a blood vessel, and the system will instantly highlight the vessel contour.

It should be appreciated that the presently disclosed inventions may be extended such that, rather than generate merely a synthesized 2D image and associated index/guidance map, the mapping concepts described herein may be extended to generate a fully mapped 3D volume, with each of the voxels in the mapped volume storing information related to the associated tomosynthesis slices(s) sourcing the particular voxel. For example, in one embodiment, the volume may be projected onto a fixed coordinate system, regardless of the actual volume of the breast. Projecting the volume to a fixed coordinate system in this manner facilitates processing of the image data, in particular, simplifying the correlation of voxels obtained during different acquisitions. For example, facilitating correlation of voxels in a 3D volume obtained from a CC acquisition of a breast with voxels in a volume obtained from an MLO acquisition of the same breast. In such an arrangement, one or more 3D maps may be provided, for example, to map from voxels in one slice of a 3D volume acquired via CC to one or more corresponding voxels in another volume, for example acquired via an MLO view. Such an arrangement facilitates comparison of slices obtained from different acquisitions that relate to a similar feature of interest within the breast volume, essentially permitting the medical professional to obtain a multi-planar review of a region of interest.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. Thus the above specific embodiments are illustrative, and many variations can be introduced on these embodiments without departing from the scope of the appended claims.

The invention claimed is:

1. A method for processing, displaying and navigating breast tissue images, comprising:
obtaining a plurality of 2D and/or 3D images of a patient's breast, wherein respective images of the obtained plurality of images contain one or more regions defined by X,Y coordinate locations that are common for multiple images of the plurality;
generating a synthesized 2D image of the patient's breast by importing respective regions of individual images of the plurality into a merged image, wherein an image from which a respective region is imported into the merged image comprises a source image for that region, and wherein the imported regions are selected to be incorporated into the merged image at X,Y coordinate locations corresponding to X,Y coordinate locations of the respective regions in their source image based upon a comparison of one or more attributes of the respective region in each image of the plurality that contains the respective region.

2. The method of claim 1, further comprising displaying the synthesized 2D image.

3. The method of claim 2, further comprising
receiving a user command, or otherwise detecting through a user interface, a user selection or other indication of a-region or of an object at least partially contained in said region in the displayed synthesized 2D image; and
displaying at least a portion of one or more source images of the user selected or indicated region or object.

4. The method of claim 3, further comprising generating an index map comprising identifying information of user selected images of the plurality of 2D and/or 3D images that are source images of regions and/or objects displayed in the synthesized 2D image.

5. The method of claim 3, wherein the user selected or indicated object or region is automatically highlighted in the displayed synthesized 2D image and/or in the displayed at least portions of the one or more corresponding source image.

6. The method of claim 5, wherein the object or region is highlighted in response to a further received user command or to certain user activity detected through the user interface.

7. The method of claim 5, wherein the object or region is highlighted by a contour line representing a boundary of the highlighted object or region.

8. The method of claim 5, wherein the object or region is highlighted in a manner indicating that the highlighted object or region is or contains a specified type of tissue structure.

9. The method of claim 1, wherein one of each of said one or more common regions is imported from the plurality of images into the merged image.

10. The method of claim 1, wherein the plurality of 2D and/or 3D images of a patient's breast comprises acquired or synthesized X,Y coordinate slices at differing z axis locations of the breast, the images having one or more corresponding X,Y coordinate locations.

11. The method of claim 1, wherein at least one of the one or more attributes is user selected.

12. The method of claim 1, wherein the plurality of 2D and/or 3D images is selected from a group consisting of tomosynthesis projection images, tomosynthesis reconstruction slices, mammography images, contrast enhanced mammography images, synthesized 2D images, and combinations thereof.

13. A method for processing, displaying and navigating breast tissue images, comprising:
obtaining a plurality of tomosynthesis images comprising volumetric image data of a patient's breast, wherein respective tomosynthesis images of the plurality contain one or more regions defined by X,Y coordinate locations that are common for multiple tomosynthesis images of the plurality;
importing one or more objects and/or regions from the tomosynthesis images into a synthesized 2D image based upon a comparison of one or more attributes of the respective region between respective tomosynthesis images that contain the one or more objects and/or regions, wherein an image from which respective object or region is imported into the synthesized 2D image comprises a source image for that object or region;
displaying the synthesized 2D image;
receiving a user command, or otherwise detecting through a user interface, a user selection or other indication of an object or region in the synthesized 2D image; and
displaying at least a portion of one or more tomosynthesis images from the plurality, including a source image of the user selected or indicated object or region.

14. The method of claim 13, further comprising generating an index map, the index map comprising identifying information of selected tomosynthesis images of the plurality that are source images or that otherwise contain a most similar representation of regions and/or objects in the synthesized 2D image.

15. The method of claim 13, wherein the user selected or indicated object or region is automatically highlighted in the displayed synthesized 2D image and/or in the displayed at least portions of the one or more corresponding source image.

16. The method of claim 15, wherein the object or region is highlighted in response to a further received user command or to certain user activity detected through the user interface.

17. The method of claim 15, wherein the object or region is highlighted by a contour line representing a boundary of the highlighted object or region.

18. The method of claim 15, wherein the object or region is highlighted in a manner indicating that the highlighted object or region is or contains a specified type of tissue structure.

19. A method for processing, displaying and navigating breast tissue images, comprising:
obtaining a plurality of 2D and/or 3D images of a patient's breast, wherein respective images of the obtained plurality of images contain one or more regions defined by X,Y coordinate locations that are common for multiple images of the plurality;
importing respective regions from the obtained plurality of images into a synthesized 2D image, wherein an image from which a respective region is imported into the synthesized 2D image comprises a source image for that region, the imported regions are incorporated into the merged image at X,Y coordinate locations corresponding to X,Y coordinate locations of the respective regions in their source image, and wherein one of each said regions is imported from the plurality of images into the synthesized 2D image based upon a comparison of one or more attributes of the respective region in each image that contains the respective region;

displaying the synthesized 2D image;

detecting through a user interface a location of a user movable input device in the displayed synthesized 2D image; and concurrently displaying a respective source image of a tissue structure or region that corresponds to a given location of a user movable input device in the displayed synthesized 2D image.

20. The method of claim 19, wherein the plurality of 2D and/or 3D images is selected from a group consisting of tomosynthesis projection images, tomosynthesis reconstruction slices, mammography images, contrast enhanced mammography images, synthesized 2D images, and combinations thereof.

\* \* \* \* \*